United States Patent [19]
Howard

[11] Patent Number: 5,990,125
[45] Date of Patent: Nov. 23, 1999

[54] NK-1 RECEPTOR ANTAGONISTS FOR THE TREATMENT OF CANCER

[75] Inventor: Harry Ralph Howard, Bristol, Conn.

[73] Assignee: Pfizer Inc., New York, N.Y.

[21] Appl. No.: 08/786,128

[22] Filed: Jan. 17, 1997

Related U.S. Application Data

[60] Provisional application No. 60/010,232, Jan. 19, 1996.

[51] Int. Cl.$^6$ ..................................................... A61K 31/44
[52] U.S. Cl. ............................................................. 514/305
[58] Field of Search ............................................. 514/305

[56] References Cited

FOREIGN PATENT DOCUMENTS 9520575  8/1995  WIPO .

OTHER PUBLICATIONS

Bunn, et al., Cancer Research, vol. 54, pp. 3602–3610 (1994).
Cascieri, et al., Journal of Biological Chemistry, vol. 258, p. 5158 (1983).
Cummings, et al., J. Pharm. Biomed. Anal., 12(6), pp. 811–819 (1994).
Elliott, et al., Expert Opinion on Therapeutic Patents, vol. 7(1), pp. 43–54 (UK 1997).
Goso, et al., European Journal of Pharmacology, vol. 254, pp. 221–227 (1994).
Kucharczyk, N., Expert Opinion on Investigational Drugs, vol. 4(4), pp. 229–311 (UK 1995).
Ladduwahetty, et al., Med. Chem., 39, pp. 2907–2914 (1996).
Oleynek, et al., The Journal of Antibiotics, vol. 47(4), pp. 339–410 (1994).
Orosz, et al., International Journal of Cancer, vol. 60, pp. 82–87 (1995).
Snider, et al., Science, 251, pp. 435–437 (1991).
Swain, et al., Biorg. Med. Chem. Lett., 4(18), pp. 2161–2164 (1994).
Villablanca, et al., Circ. Res., 75(6), pp. 1113–1120 (1994).

*Primary Examiner*—Jerome D. Goldberg
*Attorney, Agent, or Firm*—Peter C. Richardson; Paul H. Ginsburg; Mark Dryer

[57] ABSTRACT

The present invention relates to the use of certain NK-1 receptor antagonists (e.g., substance P receptor antagonists) to treat cancer patients, particularly cancer patients afflicted with a small cell lung carcinoma, APUDoma, astrocytoma, neuroendocrine tumor or extrapulmonary small cell carcinoma.

1 Claim, No Drawings

NK-1 RECEPTOR ANTAGONISTS FOR THE TREATMENT OF CANCER

This application claims the benefit of U.S. Provisional Application No. 60/010,232 filed Jan. 19, 1996.

The present invention relates to the use of certain NK-1 receptor antagonists, (including certain substance P receptor antagonists) to treat cancer patients afflicted with a small cell lung carcinoma, APUDoma, astrocytoma, neuroendocrine tumor or extrapulmonary small cell carcinoma.

Antal Orosz, et al, *International Journal of Cancer*, 1995, 60, 82–87, describe the use of a variety of peptidic substance P antagonists to inhibit the proliferation of small cell lung carcinoma, (e.g., in the cell line designated NCl-H69). Paul Bunn et al., *Cancer Research*, 1994, 54, 3602–3610, describe another series of substance P antagonists which are also peptidic and which are capable of inhibiting in vitro growth of a number of small cell lung carcinoma cell lines (e.g., those designated NCl-H510, NCl-H345 and SHP-77).

SUMMARY OF THE INVENTION

The present invention relates to a method of treating cancer in a mammal, including a human, comprising administering to such mammal a therapeutically effective amount of an NK-1 receptor antagonist selected from the compounds described below.

"Treating cancer", as used herein, means inhibiting or controlling the proliferation of a small cell lung carcinoma, APUDoma, neuroendocrine tumor, extrapulmonary small cell carcinoma or astrocytoma.

A "therapeutically effective amount", as used herein, means an amount effective in treating cancer, as defined immediately above.

An "astrocytoma" is a tumor composed of astrocytes. Astrocytes are neuroglial cells of ectodermal origin, characterized by fibrous, protoplasmic or plasmatofibrous processes.

APUDomas are tumors composed of APUD (amine precursor uptake and decarboxylation) cells. APUD cells are found scattered throughout the body (e.g., in the chromaffin system, hypothalamus, hypophysis, thyroid, parathyroids, lungs, gastrointestinal tract and pancreas) and are apparently unrelated but for sharing certain cytochemical and ultrastructural characteristics. They synthesize structurally related peptides (usually biogenic amines) that function as hormones or neurotransmitters (e.g., epinephrine, norepinephrine, dopamine, serotonin, enkalphalin, somatostatin, neurotensin and substance P). ADUP cells concentrate the amino acid precursors of these amines and decarboxylate them to their respective amines.

More specifically, this invention relates to a method of treating cancer in a mammal, including a human, comprising administering to such mammal a therapeutically effective amount of an NK-1 receptor antagonist that is a compound of the formula

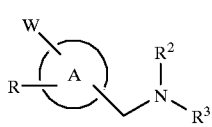

Ia

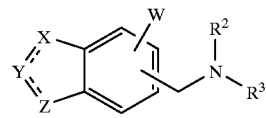

Ib

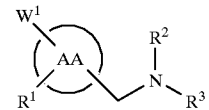

Ic

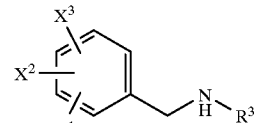

Id

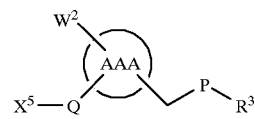

Ie wherein A is a ring system selected from phenyl, naphthyl, thienyl, dihydroquinolinyl, quinolinyl and indolinyl, and wherein the sidechain containing $NR^2R^3$ is attached to a carbon atom of ring system A;

AA is an aryl group selected from phenyl, naphthyl, thienyl, quinolinyl, dihydroquinolinyl and indolinyl, and wherein the sidechain containing $NR^2R^3$ is attached to a carbon atom of AA;

AAA is an aryl group selected from phenyl, naphthyl, thienyl, dihydroquinolinyl, quinolinyl and indolinyl, and wherein the —$CH_2PR^3$ sidechain is attached to a carbon atom of ring AAA;

P is $NR^2$, O, S, SO or $SO_2$;

Q is $SO_2$, NH,

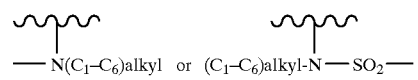

wherein the point of attachment of said

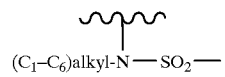

to ring AAA is the nitrogen atom and the point of attachment to $X^5$ is the sulfur atom;

$W^1$ and $W^2$ are selected, independently, from hydrogen, halo, $(C_1-C_6)$ alkyl, S-$(C_1-C_3)$alkyl, and $(C_1-C_6)$ alkoxy optionally substituted with from one to three fluorine atoms;

W is hydrogen, $(C_1-C_6)$ alkyl optionally substituted with from one to three fluorine atoms, —$S(O)_v$-$(C_1-C_6)$ alkyl wherein v is zero, one or two, halo or $(C_1-C_6)$ alkoxy optionally substituted with from one to three fluorine atoms;

$X^1$ is hydrogen, $(C_1-C_{10})$ alkoxy optionally substituted with from one to three fluorine atoms or $(C_1-C_{10})$ alkyl optionally substituted with from one to three fluorine atoms;

$X^2$ and $X^3$ are independently selected from hydrogen, halo, nitro, $(C_1-C_{10})$ alkyl optionally substituted with from one to three fluorine atoms, $(C_1-C_{10})$ alkoxy optionally substituted with from one to three fluorine atoms, hydroxy, phenyl, cyano, amino, $(C_1-C_6)$-alkylamino, di-$(C_1-C_6)$ alkylamino,

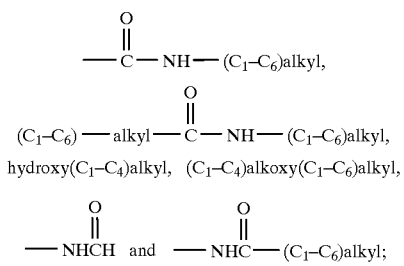

$X^5$ is a four to six membered heterocyclic ring containing from one to four heteroatoms selected from sulfur, nitrogen and oxygen (e.g., thiazolyl, pyrrolyl, thienyl, triazolyl, tetrazolyl, oxazolyl, oxadiazolyl, thiadiazolyl or imidazolyl), wherein said heterocyclic ring may optionally be substituted with from one to three substituents, preferably with from zero to two substituents, independently selected from phenyl, $(C_1-C_6)$alkyl optionally substituted with from one to three fluorine atoms, $(C_1-C_6)$alkoxy optionally substituted with from one to three fluorine atoms and halo;

R is a 4, 5 or 6 membered heterocyclic ring containing from one to four heteroatoms selected from oxygen, nitrogen and sulfur (e.g., thiazolyl, azetidinyl, pyrrolyl, pyrazolyl, 1,2,3-triazolyl, 1,2,4-triazolyl, isothiazolyl, imidazolyl, isoxazolyl, or oxazolyl) wherein said heterocyclic ring may contain from zero to three double bonds and may optionally be substituted with one or more substituents, preferably one or two substituents, independently selected from $(C_1-C_6)$ alkyl optionally substituted with from one to three fluorine atoms and $(C_1-C_6)$ alkoxy optionally substituted with from one to three fluorine atoms;

$R^1$ is selected from amino, $(C_1-C_6)$alkylamino, di-$(C_1-C_6)$alkylamino, —S(O)$_v$-$(C_1-C_{10})$-alkyl wherein v is zero, one or two, —S(O)$_v$-phenyl wherein v is zero, one or two, —S(O)$_v$-benzyl wherein v is zero, one or two, —O-phenyl, —O-benzyl, -SO$_2$NR$^4$R$^5$ wherein each of R$^4$ and R$^5$ is, independently, $(C_1-C_6)$alkyl, or R$^4$ and R$^5$, together with the nitrogen to which they are attached, form a saturated ring containing one nitrogen and from 3 to 6 carbons,

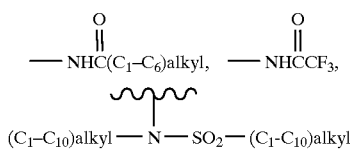

wherein one or both of the alkyl moieties may optionally be substituted with from one to three fluorine atoms,

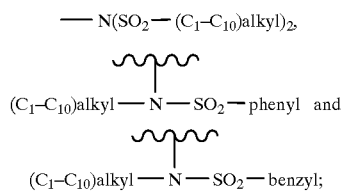

and wherein any of the phenyl moieties in the foregoing $R^1$ groups may optionally be substituted with from one to three substituents independently selected from $(C_1-C_4)$ alkyl, $(C_1-C_4)$ alkoxy and halo;

or $R^1$ is phenyl substituted with a group having the formula

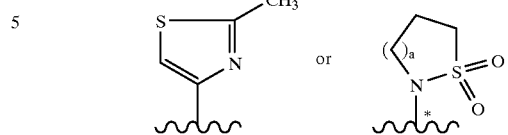

wherein a is 0, 1 or 2 and the asterisk represents a bond to a position meta to the $R^2R^3NCH_2$ side chain;

the dotted lines in formula Ib represent that one of the X-Y and Y-Z bonds may optionally be a double bond;

X is selected from =CH—, —CH$_2$—, —O—, —S—, —SO—, —SO$_2$—, —N(R$^4$)—, —NH—, =N—, —CH[(C$_1$-C$_6$)alkyl]—, =C[(C$_1$-C$_6$)alkyl]—, —CH(C$_6$H$_5$)— and =C(C$_6$H$_5$)—;

Y is selected from C=O, C=NR$^4$, C=S, =CH—, —CH$_2$—, =C[(C$_1$-C$_6$)alkyl]—, —CH[(C$_1$-C$_6$)alkyl]—, =C(C$_6$H$_5$)—, —CH(C$_6$H$_5$)—, =N—, —NH—, —N(R$^4$)—, =C(halo)—, =C(OR$^4$)—, =C(SR$^4$)—, =C(NR$^4$)—, —O—, —S— and SO$_2$, wherein the phenyl moieties of said =C(C$_6$H$_5$)— and —CH(C$_6$H$_5$)— may optionally be substituted with from one to three substituents independently selected from trifluoromethyl and halo, and wherein the alkyl moieties of said =[(C$_1$-C$_6$)alkyl]— and —CH[C$_1$-C$_6$)alkyl]— may optionally be substituted with from one to three fluorine atoms;

Z is selected from =CH—, —CH$_2$—, =N—, —NH—, —S—, —N(R$^4$)—, =C(C$_6$H$_5$)—, —CH(C$_6$H$_5$)—, =C[(C$_1$-C$_6$)alkyl]— and —CH[(C$_1$-C$_6$)alkyl]—;

or X, Y and Z, together with the two carbon atoms shared between the benzo ring and the XYZ ring, form a fused pyridine or pyrimidine ring;

$R^4$ is $(C_1-C_6)$ alkyl or phenyl, and each occurrence of $R^4$ is independent of other occurrences of $R^4$ in the same molecule;

$R^2$ is hydrogen or —CO$_2$(C$_1$-C$_{10}$)alkyl;

$R^3$ is selected from

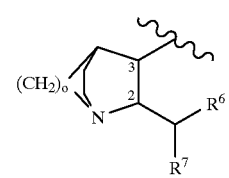

II

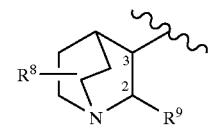

III

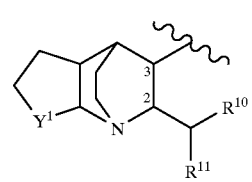

IV

-continued

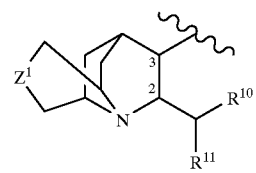
V

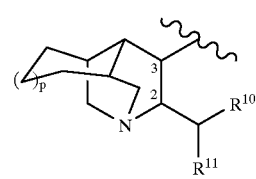
VI

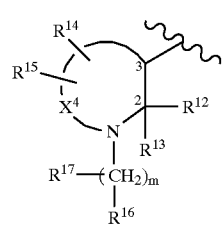
VII

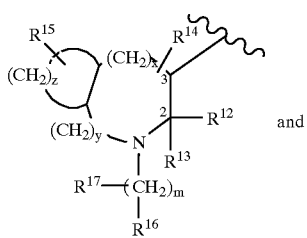
and

VIII

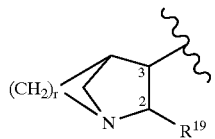
IX wherein R⁶ and R¹⁰ are independently selected from furyl, thienyl, pyridyl, indolyl, biphenyl and phenyl, wherein said phenyl may optionally be substituted with one or two substituents independently selected from halo, $(C_1-C_{10})$ alkyl optionally substituted with from one to three fluorine atoms, $(C_1-C_{10})$ alkoxy optionally substituted with from one to three fluorine atoms, carboxy, benzyloxycarbonyl and $(C_1-C_3)$ alkoxy-carbonyl;

R⁷ is selected from $(C_3-C_4)$ branched alkyl, $(C_5-C_6)$ branched alkenyl, $(C_5-C_7)$ cycloalkyl, and the radicals named in the definition of R⁶;

R⁸ is hydrogen or $(C_1-C_6)$ alkyl;

R⁹ and R¹⁹ are independently selected from phenyl, biphenyl, naphthyl, pyridyl, benzhydryl, thienyl and furyl, and R⁹ and R¹⁹ may optionally be substituted with from one to three substituents independently selected from halo, $(C_1-C_{10})$ alkyl optionally substituted with from one to the fluorine atoms and $(C_1-C_{10})$ alkoxy optionally substituted with from one to three fluorine atoms;

Y¹ is $(CH_2)_I$ wherein I is an integer from one to three, or Y¹ is a group of the formula J

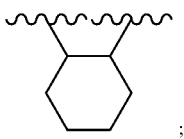
J

Z¹ is oxygen, sulfur, amino, $(C_1-C_3)$alkylamino or $(CH_2)_k$ wherein k is zero, one or two;

x is an integer from zero to four;

y is an integer from zero to four;

z is an integer from one to six, wherein the ring containing $(CH_2)_z$ may contain from zero to three double bonds, and one of the carbons of $(CH_2)_z$ may optionally be replaced by oxygen, sulfur or nitrogen;

o is two or three;

p is zero or one;

r is one, two or three;

R¹¹ is thienyl, biphenyl or phenyl optionally substituted with one or two substituents independently selected from halo, $(C_1-C_{10})$ alkyl optionally substituted with from one to three fluorine atoms and $(C_1-C_{10})$ alkoxy optionally substituted with from one to three fluorine atoms;

X⁴ is $(CH_2)_q$ wherein q is an integer from 1 to 6, and wherein any one of the carbon—carbon single bonds in said $(CH_2)_q$ may optionally be replaced by a carbon—carbon double bond, and wherein any one of the carbon atoms of said $(CH_2)_q$ may optionally be substituted with R¹⁴, and wherein any one of the carbon atoms of said $(CH_2)_q$ may optionally be substituted with R¹⁵;

m is an integer from 0 to 8, and any one of the carbon-carbon single bonds of $(CH_2)_m$, wherein both carbon atoms of such bond are bonded to each other and to another carbon atom in the $(CH_2)_m$ chain, may optionally be replaced by a carbon—carbon double bond or a carbon—carbon triple bond, and any one of the carbon atoms of said $(CH_2)_m$ having the requisite available bonding sites may optionally be substituted with R¹⁷;

R¹² is a radical selected from hydrogen, $(C_1-C_6)$ straight or branched alkyl, $(C_3-C_7)$cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl-$(C_2-C_6)$alkyl, benzhydryl and benzyl, wherein the point of attachment on R¹² is a carbon atom unless R¹² is hydrogen, and wherein each of said aryl and heteroaryl groups and the phenyl moieties of said benzyl, phenyl-$(C_2-C_6)$alkyl and benzhydryl may optionally be substituted with one or more substituents independently selected from halo, nitro, $(C_1-C_{10})$alkyl optionally substituted with from one to three fluorine atoms, $(C_1-C_{10})$alkoxy optionally substituted with from one to three fluorine atoms, amino, hydroxy-$(C_1-C_6)$alkyl, $(C_1-C_6)$ alkoxy-$(C_1-C_6)$alkyl, $(C_1-C_6)$alkylamino,

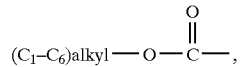

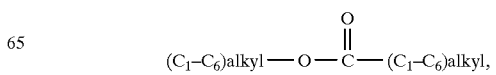

-continued

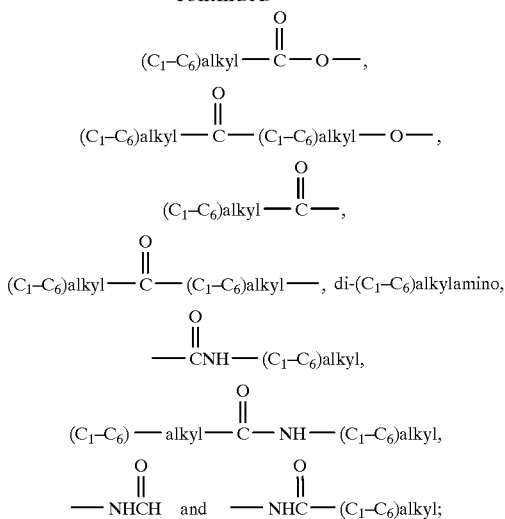

and wherein one of the phenyl moieties of said benzhydryl may optionally be replaced by naphthyl, thienyl, furyl or pyridyl;

$R^{13}$ is hydrogen, phenyl or $(C_1-C_6)$alkyl;

or $R^{12}$ and $R^{13}$ together with the carbon to which they are attached, form a saturated carbocyclic ring having from 3 to 7 carbon atoms wherein one of said carbon atoms that is neither the point of attachment of the spiro ring nor adjacent to it may optionally be replaced by oxygen, nitrogen or sulfur;

$R^{14}$ and $R^{15}$ are each independently selected from hydrogen, hydroxy, halo, amino, oxo (=O), cyano, hydroxy-$(C_1-C_6)$alkyl, $(C_1-C_6)$alkoxy-$(C_1-C_6)$alkyl, $(C_1-C_6)$alkylamino, di-$(C_1-C_6)$alkylamino, $(C_1-C_6)$alkoxy,

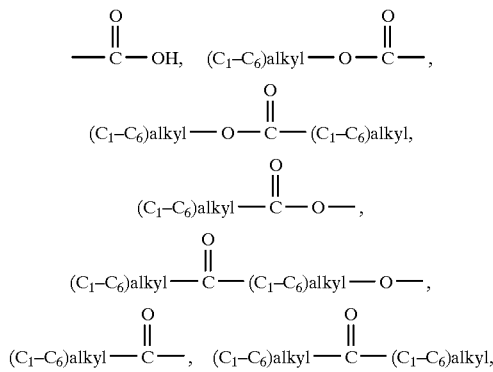

and the radicals set forth in the definition of $R^{12}$;

$R^{16}$ is

$NHCH_2R^{18}$, $SO_2R^{18}$, $GR^{20}$, $CO_2H$ or one of the radicals set forth in any of the definitions of $R^{12}$, $R^{14}$ and $R^{15}$;

$R^{17}$ is oximino (=NOH) or one of the radicals set forth in any of the definitions of $R^{12}$, $R^{14}$ and $R^{15}$; and $R^{18}$ is $(C_1-C_6)$alkyl, hydrogen, phenyl or phenyl $(C_1-C_6)$alkyl;

G is selected from the group consisting of $CH_2$, nitrogen, oxygen, sulfur and carbonyl;

$R^{20}$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyl, thienyl, and groups of the formulae

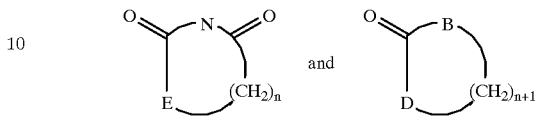

wherein B and D are selected from carbon, oxygen, and nitrogen, and at least one of B and D is other than carbon; E is carbon or nitrogen; n is an integer from 1 to 5; and any one of the carbons of the $(CH_2)_n$ or $(CH_2)_{n+1}$ may be optionally substituted with $(C_1-C_6)$alkyl or $(C_2-C_6)$ spiroalkyl, and either any two of the carbon atoms of said $(CH_2)_n$ and $(CH_2)_{n+1}$ may be bridged by a one or two carbon atom linkage, or any one pair of adjacent carbons of said $(CH_2)_n$ and $(CH_2)_{n+1}$ may form, together with from one to three carbon atoms that are not members of the carbonyl containing ring, a $(C_3-C_5)$ fused carbocyclic ring;

with the proviso that (a) when m is 0, one of $R^{16}$ and $R^{17}$ is absent and the other is hydrogen, (b) when $R^3$ is a group of the formula VIII, $R^{14}$ and $R^{15}$ cannot be attached to the same carbon atom, (c) when $R^{14}$ and $R^{15}$ are attached to the same carbon atom, then either each of $R^{14}$ and $R^{15}$ is independently selected from hydrogen, fluoro, $(C_1-C_6)$ alkyl, hydroxy-$(C_1-C_6)$alkyl and $(C_1-C_6)$alkoxy-$(C_1-C_6)$ alkyl, or $R^{14}$ and $R^{15}$, together with the carbon to which they are attached, form a $(C_3-C_6)$ saturated carbocyclic ring that forms a spiro compound with the nitrogen-containing ring to which they are attached; (d) $R^{12}$ and $R^{13}$ cannot both be hydrogen; (e) when $R^{14}$ or $R^{15}$ is attached to a carbon atom of $X^4$ of group VII or to a carbon atom of $(CH_2)_y$ of group VIII that is adjacent to the ring nitrogen, then $R^{14}$ or $R^{15}$, respectively, must be a substituent wherein the point of attachment is a carbon atom; (f) when said compound is a group of the formula Id or a group of the formula Ic or Ie wherein AA or AAA, respectively, is phenyl optionally substituted with 1, 2 or 3 groups selected from $(C_1-C_6)$alkyl, trifluoromethyl, halo, cyano, nitro, $(C_1-C_6)$alkoxy, trifluoromethoxy, and —S(O)$_v$—$(C_1-C_{10})$alkyl wherein v is zero, one or two, and $R^3$ is a group of the formula VII wherein $R^{13}$ is hydrogen and $R^{12}$ is phenyl, naphthyl, thienyl, furyl, pyridyl, thiazolyl, tetrazolyl, quinolyl, benzhydryl or benzyl, and $R^{12}$ is optionally substituted with $(C_1-C_6)$alkyl, trifluoromethyl, $(C_1-C_6)$alkoxy or halo, then at least one of $R^{14}$ and $R^{15}$ must be other than hydrogen, $(C_1-C_6)$alkyl, oxo, halo, —COOH, —COO$(C_1-C_6)$alkyl or phenyl optionally substituted with $(C_1-C_6)$alkyl, halo ortri-fluoromethyl; and (g) neither $R^{14}$, $R^{15}$, $R^{16}$ nor $R^{17}$ can form a ring with $R^{13}$;

or a pharmaceutically acceptable salt of such compound.

The fused bicyclic nucleus of compounds of the formula Ib to which W and the —CN$_2$NR$^2$R$^3$ sidechain are attached may be, but is not limited to one of the following groups: benzoxazolyl, benzothiazolyl, benzimidazolyl, benzisoxazolyl, benzisothiazolyl, indazolyl, indolyl, isoquinolinyl, benzofuryl, benzothienyl, oxindolyl, benzoxazolinonyl, benzothiazolinonyl, benzimidazolinonyl, benzimidazoliniminyl, dihydrobenzothienyl-S,S-dioxide, benzotriazolyl, benzothiadiazolyl, benzoxadiazolyl, and quinazolinyl.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "one or more substituents," as used herein, includes from one to the maximum number of substituents possible based on the number of available bonding sites.

More specific embodiments of this invention relate to the above method of treating cancer, wherein the NK-1 receptor antagonist is a compound as defined in any of paragraphs (1) through (42) below, or a pharmaceutically acceptable salt of such compound.

(1) A compound of the formula Ia or Ib wherein the substituents at positions "2" and "3" of the nitrogen containing ring of $R^3$ are in a cis configuration. (When $R^3$ is a group of the formula VII or VIII, "a cis configuration", as used herein, means that the non-hydrogen substituent at position "3" is cis to $R^{12}$).

(2) A compound of the formula Ia wherein $R^3$ is a group of the formula III, VII or IX; $R^2$ is hydrogen; A is phenyl or indolinyl; W is $(C_1-C_3)$alkoxy optionally substituted with from one to five fluorine atoms; and R is thiazolyl, imidazolyl, thiadiazolyl, pyrrolyl or oxazolyl, and R may optionally be substituted with one or two $(C_1-C_3)$ alkyl moieties.

(3) A compound of the formula Ib wherein $R^3$ is a group of the formula III, VII or IX; $R^2$ is hydrogen; the fused bicyclic ring system to which W and the —$CH_2NR^2R^3$ sidechain are attached is benzoxazolyl, benzisoxazolyl, benzothiazolyl or benzimidazolyl; and W is $(C_1-C_6)$alkoxy optionally substituted with from one to five fluorine atoms.

(4) A compound as defined in paragraph 1, 2 or 3 above wherein: (a) $R^3$ is a group of the formula III and $R^9$ is benzhydryl; (b) $R^3$ is a group of the formula VII, $R^{12}$ is phenyl, each of $R^{13}$, $R^{14}$, $R^{15}$ and $R^{16}$ is hydrogen, m is zero and $X^4$ is —$(CH_2)_3$—; or (c) $R^3$ is a group of the formula IX, r is two and $R^{19}$ is benzhydryl.

(5) A compound of the formula Ia wherein: (a) $R^3$ is a group of the formula III wherein the substituents at positions "2" and "3" of the nitrogen containing ring are in the cis configuration, $R^9$ is benzhydryl and A is phenyl; or (b) $R^3$ is a group of the formula VII wherein $R^{12}$ and the substituent at position "3" of the nitrogen containing ring are in the cis configuration, A is phenyl, $R^{12}$ is phenyl, each of $R^2$, $R^{13}$, $R^{14}$, $R^{15}$ and $R^{16}$ is hydrogen, m is zero, W is methoxy or isopropoxy, $X^4$ is —$(CH_2)_3$— and R is thiazolyl, imidazolyl, pyrrolyl, oxazolyl or thiadiazolyl.

(6) A compound of the formula Ib wherein $R^3$ is a group of the formula IX wherein the substituents at positions "2" and "3" of the nitrogen containing ring are in the cis configuration, $R^{19}$ is benzhydryl, r is two and the fused bicyclic ring system to which W and the —$CH_2NR^2R^3$ sidechain are attached is benzisoxazolyl or benzothiazolyl.

(7) A compound of the formula Ib wherein $R^3$ is a group of the formula IX, $R^{19}$ is benzhydryl, the fused bicyclic ring system to which W and the —$CH_2NR^2R^3$ sidechain are attached is benzoxazolyl, and W is methoxy.

(8) A compound of the formula Ib wherein $R^3$ is a group of the formula VII, $R^{12}$ is phenyl, each of $R^{13}$, $R^{14}$, $R^{15}$ and $R^{16}$ is hydrogen, m is zero, $X^4$ is —$(CH_2)_3$—, and the fused bicyclic ring system to which W and the —$CH_2NR^2R^3$ sidechain are attached is benzothiazolyl, benzoxazolyl or benzimidazolyl.

(9) A compound of the formula Ia wherein $R^3$ is a group of the formula VII, each of $R^{13}$, $R^{14}$, $R^{15}$ and $R^{16}$ is hydrogen, m is zero, $X^4$ is —$(CH_2)_3$—, A is phenyl, W is methoxy, and R is selected from thiazolyl, imidazolyl, thiadiazolyl and isoxazolyl.

(10) A compound of the formula Ic, wherein $R^3$ is a group of the formula II, III, VII or IX; $R^2$ is hydrogen; ring AA is phenyl or indolinyl; $W^1$ is $(C_1-C_3)$alkoxy optionally substituted with from one to three fluorine atoms; and $R^1$ is $S(O)_v$-$(C_1-C_{10})$alkyl wherein v is zero, one or two, $S(O)_v$-aryl wherein v is zero, one or two, —O-aryl,

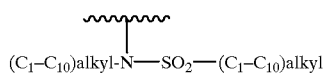

wherein one or both of the alkyl moieties may optionally be substituted with from one to three fluorine atoms, —$N(SO_2$—$(C_1-C_{10})$alkyl$)_2$ or

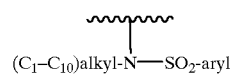

wherein said aryl is phenyl or benzyl and may optionally be substituted with from one to three substituents independently selected from $(C_1-C_4)$alkyl, $(C_1-C_4)$alkoxy and halo.

(11) A compound as defined in paragraph 10 above, wherein $R^3$ is a group of the formula II, o is two, and each $R^6$ and $R^7$ is phenyl.

(12) A compound as defined in paragraph 10 above, wherein $R^3$ is a group of the formula VII, each of $R^{13}$, $R^{14}$, $R^{15}$ and $R^{16}$ is hydrogen, $R^{12}$ is phenyl, m is zero and $X^4$ is —$(CH_2)_3$—.

(13) A compound as defined in paragraph 10 above, wherein $R^3$ is a group of the formula IX, $R^{19}$ is benzhydryl and r is two.

(14) A compound as defined in paragraph 10 above, wherein $R^3$ is a group of the formula III, $R^8$ is other than hydrogen and $R^9$ is benzyhydryl.

(15) A compound of the formula Ic wherein the substituents at positions "2" and "3" of the nitrogen containing ring of $R^3$ are in the cis configuration.

(16) A compound of the formula 1c wherein $R^3$ is a group of the formula II wherein the substituents at positions "2" and "3" of the nitrogen containing ring are in the cis configuration, o is two, each of $R^6$ and $R^7$ is phenyl and ring AA is phenyl or indolinyl.

(17) A compound of the formula Ic wherein $R^3$ is a group of the formula III wherein the substituents at positions "2" and "3" of the nitrogen containing ring are in the cis configuration, $R^8$ is other than hydrogen, $R^9$ is benzhydryl and ring AA is phenyl.

(18) A compound of the formula Ic wherein $R^3$ is a group of the formula VII wherein $R^{12}$ and the substituent at position "3" of the nitrogen containing ring are in the cis configuration, ring AA is phenyl, $R^{12}$ is phenyl, each of $R^2$, $R^{13}$, $R^{14}$, $R^{15}$ and $R^{16}$ is hydrogen, m is zero, $X^4$ is —$(CH_2)_2$— or —$(CH_2)_3$— and $R^1$ is selected from $S(O)_v$-$(C_1-C_{10})$ alkyl wherein v is zero, one or two,

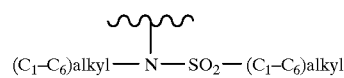

and di-$(C_1-C_6)$alkylamino.

(19) A compound as defined in paragraph 18 above, wherein $X^4$ is —$(CH_2)_2$— and $W^1$ is $(C_1-C_6)$ alkoxy optionally substituted with from one to three fluorine atoms.

(20) A compound as defined in paragraph 18 above, wherein $X^4$ is —$(CH_2)_3$— and $W^1$ is $(C_1-C_6)$ alkoxy optionally substituted with from one to three fluorine atoms.

(21) A compound of the formula Ic, wherein $R^3$ is a group of the formula IX wherein the substituents at positions "2" and "3" of the nitrogen containing ring are in the cis configuration, r is two and $R^{19}$ is benzhydryl.

(22) A compound as defined in paragraph 21 above, wherein ring AA is phenyl, $W^1$ is $(C_1-C_6)$ alkoxy optionally substituted with from one to three fluorine atoms and $R^1$ is selected from —$S(O)_v$-$(C_1-C_{10})$alkyl wherein v is zero, one or two, $(C_1-C_6)$alkylamino, di-$(C_1-C_6)$ alkylamino and

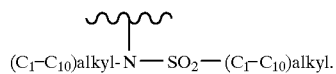

(23) A compound as defined in paragraph 15 above, wherein ring AA is phenyl, $W^1$ is $(C_1-C_6)$alkoxy optionally substituted with from one to three fluorine atoms, and $R^1$ is selected from —$S(O)_v$-$(C_1-C_{10})$alkyl wherein v is zero, one or two, and

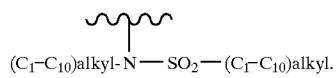

(24) A compound as defined in paragraph 15 above, wherein ring AA is phenyl, $W^1$ is $(C_1-C_6)$alkoxy optionally substituted with from one to three fluorine atoms, and $R^1$ is selected from amino, $(C_1-C_6)$alkylamino and di-$(C_1-C_6)$ alkylamino.

(25) A compound as defined in paragraph 12 above, wherein ring AA is phenyl and $R^1$ is selected from —$S(O)_v$-$(C_1-C_{10})$alkyl wherein v is zero, one or two, and

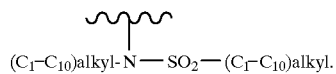

(26) A compound of the formula Io wherein $R^3$ is a group of the formula III, ring AA is phenyl, $W^1$ is $(C_1-C_6)$alkoxy optionally substituted with from one to three fluorine atoms, and $R^1$ is selected from amino, $(C_1-C_6)$alkylamino or di-$(C_1-C_6)$alkylamino.

(27) A compound as defined in paragraph 24 above, wherein $W^1$ is attached at the "2" position of ring M and $R^1$ is attached at the "5" position of ring AA, relative to the point of attachment of the $NR^2R^3$ containing side chain.

(28) A compound as defined in paragraph 25 above, wherein $W^1$ is attached at the "2" position of ring AA and $R^1$ is attached at the "5" position of ring AA, relative to the point of attachment of the $NR^2R^3$ containing side chain.

(29) A compound as defined in paragraph 26 above, wherein $W^1$ is attached at the "2" position of ring AA and $R^1$ is attached at the "5" position of ring AA, relative to the point of attachment of the $NR^2R^3$ containing side chain.

(30) A compound as defined in paragraph 23 above, wherein $W^1$ is attached at the "2" position of ring AA and $R^1$ is attached at the "5" position of ring AA, relative to the point of attachment of the $NR^2R^3$ containing side chain.

(31) A compound as defined in paragraph 13 above, wherein ring AA is phenyl, $W^1$ is selected from isopropoxy, $OCF_3$, $OCH_3$, $OCHF_2$ and $OCH_2CF_3$, and $R^1$ is selected from —$S(O)_v$-$(C_1-C_{10})$alkyl wherein v is zero, one or two, and $(C_1-C_{10})$alkyl-N-$SO_2$—$(C_1-C_{10})$alkyl.

(32) A compound of the formula Ic, wherein $R^3$ is a group of the formula VII, m is zero, each of $R^{13}$, $R^{15}$, $R^{16}$ and $R^{17}$ is hydrogen, $R^{12}$ is phenyl, $R^{14}$ is

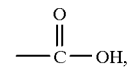

ring AA is phenyl, $W^1$ is $(C_1-C_3)$alkoxy and $R^1$ is selected from $(C_1-C_5)$alkyl, —$SCH_3$, $SO_2CH_3$, $SOCH_3$, $(C_1-C_6)$ alkylamino and di-$(C_1-C_6)$alkylamino.

(33) A compound of the formula Ic, having the formula

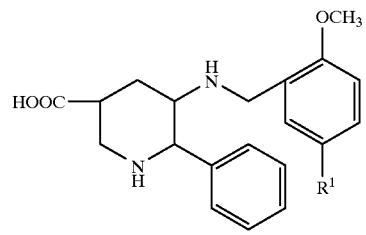

(34) A compound of the formula Id wherein $R^5$, $R^7$, $R^{10}$, $R^{11}$ and $R^{13}$ are phenyl, $R^8$ is hydrogen, $R^9$ is phenyl optionally substituted with chlorine, fluorine, $(C_1-C_6)$ alkyl optionally substituted with from one to three fluorine atoms or $(C_1-C_6)$ alkoxy optionally substituted with from one to three fluorine atoms, m is 0 and k is 3 or 4.

(35) A compound of the formula Id, wherein $R^3$ is a group of the formula II wherein o is two or three and each of $R^6$ and $R^7$ is phenyl or substituted phenyl.

(36) A compound of the formula Id, wherein $R^3$ is a group of the formula III, $R^8$ is hydrogen and $R^9$ is phenyl or substituted phenyl.

(37) A compound of the formula Id, wherein $R^3$ is a group of the formula IV wherein I is one or two and each of $R^{10}$ and $R^{11}$ is phenyl or substituted phenyl.

(38) A compound of the formula Id, wherein $R^3$ is a group of the formula V wherein k is zero or one and each of $R^{10}$ and $R^{11}$ is phenyl or substituted phenyl.

(39) A compound of the formula Id, wherein $R^3$ is a group of the formula VI wherein p is one and each of $R^{10}$ and $R^{11}$ are phenyl or substituted phenyl.

(40) A compound of the formula Id, wherein $R^3$ is a group of the formula VII wherein q is two, three or four, m is zero and $R^{12}$ is phenyl or substituted phenyl.

(41) A compound of the formula Id, wherein $R^3$ is a group of the formula VIII wherein y is zero, x is zero or one, z is three or four, m is zero and $R^{12}$ is phenyl or substituted phenyl.

(42) A compound of the formula Id wherein $R^3$ is a group of the formula VII, $R^{14}$, $R^{13}$, $R^{16}$ and $R^{15}$ are hydrogen, $R^{12}$ is phenyl, $X^1$ is 2-methoxy, $X^2$ and $X^3$ are independently selected from hydrogen, chlorine, fluorine, methyl, $(C_1-C_6)$ alkoxy and trifluoromethyl, m is 0 and q is 3 or 4.

This invention also relates to a method of treating cancer in a mammal, including a human, comprising administering to said mammal a therapeutically effective amount of an NK-1 receptor antagonist that is a compound having the formula

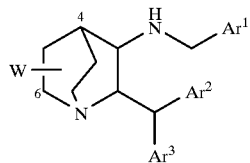

wherein W is Y or X(CH$_2$)$_n$;

Y is optionally substituted (C$_1$–C$_6$)alkyl, optionally substituted (C$_2$–C$_6$)alkenyl or optionally substituted (C$_3$–C$_8$) cycloalkyl;

X is optionally substituted (C$_1$–C$_6$)alkoxy, hydroxy, CONR$^1$R$^2$, CO$_2$R$^1$, CHR$^1$OR$^2$, CHR$^1$NR$^2$R$^3$, COR$^1$, CONR$^1$OR$^2$ or optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and n is an Integer from zero to six;

Ar$^1$, Ar$^2$ and Ar$^3$ are each, independently, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl;

and R$^1$, R$^2$ and R$^3$ are independently selected from hydrogen, optionally substituted (C$_1$–C$_6$)alkyl, optionally substituted (C$_1$–C$_6$)alkoxy, optionally substituted (C$_3$–C$_8$) cycloalkyl, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and optionally substituted (C$_3$–C$_5$) heterocyclic groups, wherein said heterocyclic groups are selected from pyrrolidino, piperidino, morpholino, piperazinyl and thiamorpholino;

and wherein the substituents on the foregoing substituted alkyl, alkenyl, cycloalkyl and alkoxy groups are independently selected from halo, nitro, amino, (C$_1$–C$_4$)alkyl, (C$_1$–C$_4$)alkoxy, trifluoromethyl and trifluoromethoxy;

and wherein the substituents on the foregoing substituted (C$_3$–C$_5$) heterocyclic groups are attached to a sulfur or nitrogen atom on the ring and are independently selected from oxygen, di-oxygen and (C$_1$–C$_4$)alkyl when attached to a ring sulfur atom, and are independently selected from oxygen and (C$_1$–C$_4$)alkyl when attached to a ring nitrogen atom;

and wherein the substituents on said substituted Ar$^1$ groups are independently selected from (C$_1$–C$_6$)alkyl optionally substituted with from one to three halo groups, (C$_1$–C$_6$)alkoxy optionally substituted with from one to three halo groups, (C$_1$–C$_6$)alkylsulfinyl, (C$_2$–C$_6$)alkenyl, (C$_1$–C$_6$) alkylthio, (C$_1$–C$_6$)alkylsulfonyl, (C$_1$–C$_6$) alkylsulfonylamino, and di-(C$_1$–C$_6$)alkylamino wherein one or both of the alkyl groups may be optionally substituted with a (C$_1$–C$_6$)alkylsulfonyl, or (C$_1$–C$_6$)alkylsulfinyl group;

and wherein the substituents on said substituted Ar$^2$ and Ar$^3$ groups are independently selected from (C$_1$–C$_4$)alkyl, (C$_1$–C$_4$)alkoxy, (C$_1$–C$_4$)alkylthio, (C$_1$–C$_4$)alkylsulfinyl, di-(C$_1$–C$_4$)alkylamino, trifluoromethyl and trifluoromethoxy; with the proviso that when Y is unsubstituted or is substituted with (C$_1$–C$_4$)alkyl, it is attached to the 4- or 6-position of the quinuclidine ring;

or a pharmaceutically acceptable salt of such compound.

Other more specific embodiments of this invention relate to the method of treating cancer described immediately above, wherein the NK-1 receptor antagonist is a compound as defined in any of paragraphs (43) through (48) below, or a pharmaceutically acceptable salt of such compound.

(43) A compound of the formula X, wherein W is X(CH$_2$)$_n$.

(44) A compound of the formula X, wherein W is Y.

(45) A compound of the formula X, wherein Ar$^1$ is substituted aryl and W is Y.

(46) A compound of the formula X, wherein Ar$^1$ is mono-, di- or tri-substituted phenyl and W is Y.

(47) A compound of the formula X, wherein Ar$^1$ is phenyl disubstituted at the 2- and 5-positions and W is Y.

(48) A compound of the formula X, wherein Ar$^1$ is para-methoxyphenyl, each of Ar$^2$ and Ar$^1$ is phenyl and W is Y.

This invention also relates to a method of treating cancer in a mammal, including a human, comprising administering to said mammal a therapeutically effective amount of an NK-1 receptor antagonist that is a compound of the formula

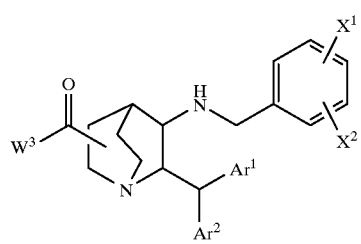

wherein X$^1$ is C$_1$–C$_5$ alkoxy or halosubstituted (C$_1$–C$_5$) alkoxy;

X$^2$ is hydrogen, halogen, (C$_1$–C$_5$)alkyl, (C$_2$–C$_5$)alkenyl, (C$_2$–C$_5$)alkynyl, (C$_1$–C$_5$)alkoxy, (C$_1$–C$_5$)alkylthio, (C$_1$–C$_5$) alkylsulfinyl, (C$_1$–C$_5$) alkylsulfonyl, halosubstituted (C$_1$–C$_5$) alkyl, halosubstituted (C$_1$–C$_5$) alkoxy, (C$_1$–C$_5$) alkylamino, dialkylamino having from 1 to 5 carbon atoms in each alkyl moiety, (C$_1$–C$_5$)alkylsulfonylamino (which may be substituted by halogen),

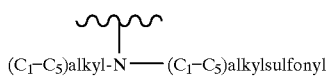

(which may be substituted by halogen in the alkylsulfonyl moiety), (C$_1$–C$_5$)alkanoylamino (which may be substituted by halogen) or

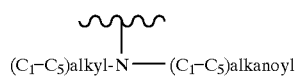

(which may be substituted by halogen in the alkanoyl moiety);

Ar$^1$ and Ar$^2$ are each, independently, thienyl, phenyl, fluorophenyl, chlorophenyl or bromophenyl;

W$^3$ is Y—(CH$_2$)$_m$—CH(R$^2$)—(CH$_2$)$_n$—NR$^1$—;

R$^1$ is hydrogen, (C$_1$–C$_5$)alkyl, benzyl or —(CH$_2$)$_p$—Y;

R$^2$ is hydrogen, (C$_1$–C$_5$)alkyl (which may be substituted by a substituent selected from the group consisting of hydroxy, amino, methylthio and mercapto), benzyl, 4-hydroxybenzyl, 3-indolylmethyl or —(CH$_2$)$_p$—Y;

Y is —CN, —CH$_2$Z or —COZ;

Z is hydroxy, amino, (C$_1$–C$_5$)alkoxy, (C$_1$–C$_5$) alkylamino or dialkylamino having from 1 to 5 carbon atoms in each alkyl moiety;

m, n and p are each, independently, 0, 1, 2 or 3; and

R$^1$ and R$^2$ may be connected to form a ring;

or a pharmaceutically acceptable salt of such compound.

The terms "halogen" or "halo" is used above for formula XV to mean fluoro, chloro, bromo or iodo.

The term "alkyl" is used above for formula XV to mean straight or branched hydrocarbon chain radicals including, but not limited to, methyl, ethyl, n-propyl, isopropyl, n-butyl, isobutyl, s-butyl, t-butyl, and the like.

The term "alkenyl" is used above for formula XV to mean straight or branched hydrocarbon chain radicals having one double bond including, but not limited to, ethenyl, 1- and 2-propenyl, 2-methyl-1-propenyl, 1- and 2-butenyl and the like.

The term "alkynyl" is used above for formula XV to mean straight or branched hydrocarbon chain radicals having one triple bond including, but not limited to, ethynyl, propynyl, butynyl and the like.

The term "alkoxy" is used above for formula XV to mean —OR$^3$ (R$^3$ is alkyl) including, but not limited to, methoxy, ethoxy, propoxy, isopropoxy, n-butoxy, isobutoxy, s-butoxy, t-butoxy and the like.

The term "alkylthio" is used above for formula XV to mean —SR$^4$ (R$^4$ is alkyl) including but not limited to, methylthio, ethylthio, n-propylthio, isopropylthio, n-butylthio, isobutylthio, s-butylthio, t-butylthio and the like.

The term "alkylsulfinyl" is used above for formula XV to mean —SOR$^5$ (R$^5$ is alkyl) including, but limited to, methylsulfinyl, ethylsulfinyl, propylsulfinyl, n-butylsulfinyl, isobutylsulfinyl, s-butylsulfinyl, t-butylsulfinyl and the like.

The term "alkylsulfonyl" is used above for formula XV to mean —SO$_2$R$^6$ (R$^6$ is alkyl) including, but limited to, methylsulfonyl, ethylsulfonyl, propylsulfonyl, n-butylsulfonyl, isobutylsulfonyl, s-butylsulfonyl, t-butylsulfonyl and the like.

The term "alkylsulfonylamino (which may be substituted by halogen)" is used above for formula XV to mean —NHSO$_2$R$^7$ (R$^7$ is alkyl which may be substituted by halogen) including, but not limited to, methylsuflonylamino, ethylsulfonylamino, trifluoromethylsulfonylamino and the like.

The term "N-alkyl-N-alkylsulfonylamino (which may be substituted by halogen in the alkylsulfonyl moiety)" is used above for formula XV to mean —N(R$^8$)SO$_2$R$^9$ (R$^8$ is alkyl and R$^9$ is alkyl which may be substituted by halogen) including, but not limited to, N-methyl-N-methyl sulfonylamino, N-ethyl-N-methylsulfonylamino, N-n-propyl-N-methylsulfonylamino, N-isopropyl-N-methylsulfonylamino, N-methyl-N-trifluoromethylsulfonylamino, N-ethyl-N-trifluoromethylsulfonylamino, N-n-propyl-N-trifluoromethylsulfonylamino, N-isopropyl-N-trifluoromethylsulfonylamino and the like.

The terms "alkylamino" and "dialkylamino" are used above for formula XV to mean —N(R$^{10}$)R$^{11}$ (R$^{10}$ is hydrogen or alkyl and R$^{11}$ is alkyl) including, but not limited to, methylamino, ethylamino, n-propylamino, isopropylamino, n-butylamino, t-butylamino, dimethylamino, diethylamino, ethylmethylamino and the like.

The term "alkanoylamino (which may be substituted by halogen)" is used above for formula XV to mean —NHCOR$^{12}$ (R$^{12}$ is alkyl which may be substituted by halogen) including, but not limited to, formylamino, acetylamino, propionylamino, butyrylamino, isobutyrylamino, trifluoroacetylamino and the like.

The term "N-alkyl-N-alkanoylamino (which may be substituted by halogen in the alkanoyl moiety)" is used above for formula XV to mean —N(R$^{13}$)COR$^{14}$ (R$^{13}$ is alkyl and R$^{14}$ is alkyl which may be substituted by halogen) including, but not limited to, N-acetyl-N-methylamino, N-acetyl-N-ethylamino, N-acetyl-N-n-propylamino, N-acetyl-N-isopropylamino, N-trifluoroacetyl-N-methylamino, N-trifluoroacetyl-N-ethylamino, N-trifluoroacetyl-N-n-propylamino, N-trifluoroacetyl-N-isopropylamino and the like;

The term "halosubstituted alkyl" is used above for formula XV to mean an alkyl radical as described above substituted with one or more halogens including, but not limited to, chloromethyl, trifluoromethyl, 2,2,2-trichloroethyl and the like.

The term "halosubstituted alkoxy" is used above for formula XV to mean an alkoxy radical as described above substituted with one or more halogens including, but not limited to, chloromethoxy, trifluoromethoxy, 2,2,2-trichloroethoxy and the like.

This invention also relates to a method of treating cancer in a mammal, including a human, comprising administering to said mammal a therapeutically effective amount of an NK-1 receptor antagonist that is a compound of the formula

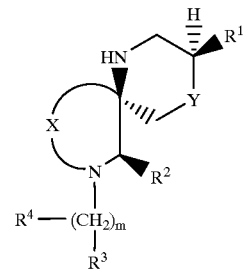

XVI wherein R$^1$ is phenyl optionally substituted with one or more substituents, preferably with from one to three substituents, independently selected from hydrogen, halo, nitro, (C$_1$–C$_{10}$) alkyl optionally substituted with from one to three fluorine atoms, (C$_1$–C$_{10}$) alkoxy optionally substituted with from one to three fluorine atoms, hydroxy, phenyl, cyano, amino, (C$_1$–C$_6$)-alkylamino, di-(C$_1$–C$_6$)alkylamino,

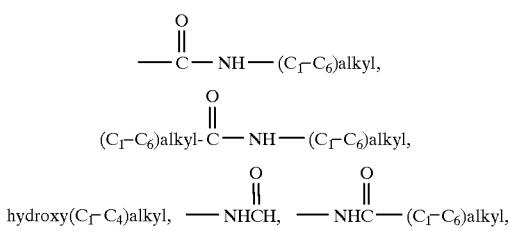

(C$_1$–C$_4$)alkoxy(C$_1$–C$_4$)alkyl, —S(O)$_v$-(C$_1$–C$_{10}$)-alkyl wherein v is zero, one or two, —S(O)$_v$-phenyl wherein v is zero, one or two, —S(O)$_v$-benzyl wherein v is zero, one or two, —O—phenyl, —O—benzyl, —SO$_2$NR$^4$R$^5$ wherein each of R$^4$ and R$^5$ is, independently, (C$_1$–C$_6$)alkyl, or R$^4$ and R$^5$, together with the nitrogen to which they are attached, form a saturated ring containing one nitrogen and from 3 to 6 carbons,

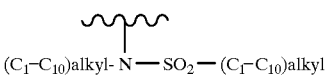

wherein one or both of the alkyl moieties may optionally be substituted with from one to three fluorine atoms, —N(SO$_2$—(C$_1$–C$_{10}$)alkyl)$_2$,

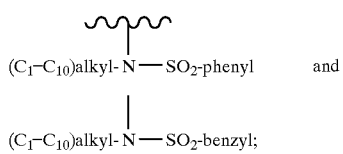

and and wherein any of the phenyl moieties in the foregoing $R^1$ groups may optionally be substituted with from one to three substituents independently selected from $(C_1-C_4)$alkyl, $(C_1-C_4)$alkoxy and halo;

or $R^1$ is phenyl substituted with a group having the formula

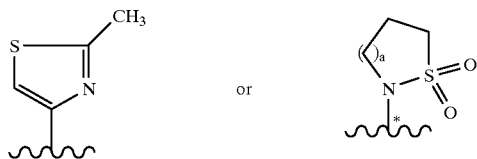

wherein a is 0, 1 or 2 and the asterisk represents a bond to a position meta to the point of attachment of $R^1$ to structure XVI;

$R^2$ is selected from $(C_1-C_6)$ straight or branched alkyl, $(C_3-C_7)$ cycloalkyl wherein one of the carbon atoms may optionally be replaced by nitrogen, oxygen or sulfur; aryl selected from biphenyl, phenyl, Indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$ alkyl, benzhydryl and benzyl, wherein each of said aryl and heteroaryl groups and the phenyl moieties of said benzyl, phenyl $(C_2-C_6)$ alkyl and benzhydryl may optionally be substituted with one or more substituents, preferably with from one to three substituents, independently selected from halo, nitro, $(C_1-C_{10})$ alkyl optionally substituted with from one to three fluorine atoms, $(C_1-C_{10})$ alkoxy optionally substituted with from one to three fluorine atoms, amino, hydroxy-$(C_1-C_6)$alkyl, $(C_1-C_6)$ alkoxy-$(C_1-C_6)$alkyl, $(C_1-C_6)$-alkylamino,

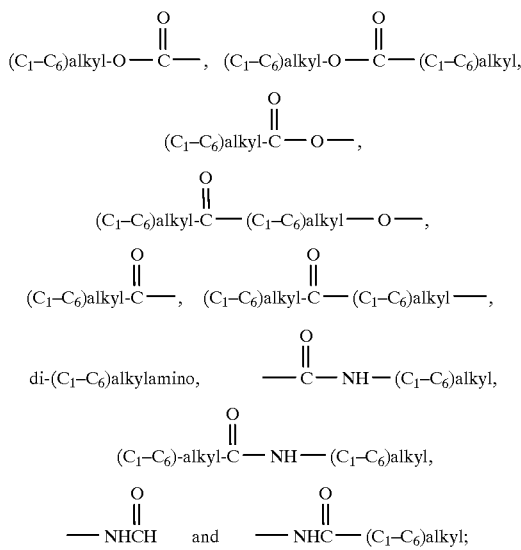

and wherein one of the phenyl moieties of said benzhydryl may optionally be replaced by naphthyl, thienyl, furyl or pyridyl;

m is an integer from 0 to 8, and any one of the carbon—carbon single bonds of $(CH_2)_m$, wherein both carbon atoms of such bond are bonded to each other and to another carbon atom in the $(CH_2)_m$ chain, may optionally be replaced by a carbon—carbon double bond or a carbon—carbon triple bond, and any one of the carbon atoms of said $(CH_2)_m$ may optionally be substituted with $R^4$;

$R^3$ is selected from

$NHCH_2R^8$, $SO_2R^8$, $AR^9$, $CO_2H$ and the radicals set forth in the definitions of $R^2$, $R^6$ and $R^7$;

A is $CH_2$, nitrogen, oxygen, sulfur or carbonyl;

$R^4$ is selected from oximino (=NOH) and the radicals set forth in the definitions of $R^2$, $R^6$ and $R^7$;

$R^8$ is $(C_1-C_6)$alkyl, hydrogen, phenyl or phenyl $(C_1-C_6)$ alkyl;

$R^9$ is a monocyclic or bicyclic heterocycle selected from the group consisting of pyrimidinyl, benzoxazolyl, 2,3-dihydro-3-oxobenzisosulfonazol-2-yl, morpholin-1-yl, thiomorpholin-1-yl, benzofuranyl, benzothienyl, Indolyl, isoindolyl, isoquinolinyl, furyl, pyridyl, isothiazolyl, oxazolyl, triazolyl, tetrazolyl, quinolyl, thiazolyl, thienyl, and groups of the formulae

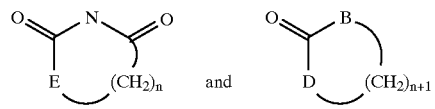

wherein B and D are selected from carbon, oxygen and nitrogen, and at least one of B and D is other than carbon; E is carbon or nitrogen; n is an integer from 1 to 5; any one of the carbon atoms of said $(CH_2)_n$ and $(CH_2)_{n+1}$ may be optionally substituted with $(C_1-C_6)$alkyl or $(C_2-C_6)$ spiroalkyl; and either any one pair of the carbon atoms of said $(CH_2)_n$ and $(CH_2)_{n+1}$ may be bridged by a one or two carbon atom linkage, or any one pair of adjacent carbon atoms of said $(CH_2)_n$ and $(CH_2)_{n+1}$ may form, together with from one to three carbon atoms that are not members of the carbonyl containing ring, a $(C_3-C_5)$ fused carbocyclic ring;

X is $(CH_2)_q$ wherein q is two or three and wherein one of the carbon—carbon single bonds in said $(CH_2)_q$ may optionally be replaced by a carbon—carbon double bond, and wherein any one of the carbon atoms of said $(CH)_q$ may optionally be substituted with $R^6$, and wherein any one of the carbon atoms of said $(CH_2)_q$ may optionally be substituted with $R^7$;

$R^6$ and $R^7$ are independently selected from hydrogen, hydroxy, halo, amino, oxo (=O), cyano, hydroxy-$(C_1-C_6)$ alkyl, $(C_1-C_6)$alkoxy-$(C_1-C_6)$alkyl, $(C_1-C_6)$alkylamino, di-$(C_1-C_6)$alkylamino,

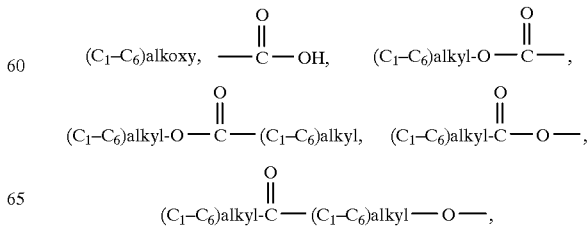

-continued

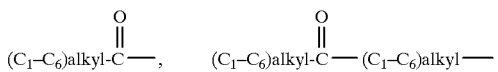

and the radicals set forth in the definition of $R^2$; and

Y is $(CH_2)_z$ wherein z is zero or one;

with the proviso that: (a) when A is —$(CH_2)$— or carbonyl, $R^9$ cannot be furyl, pyridyl, isothiazolyl, oxazolyl, triazolyl, tetrazolyl, quinolyl, thiazolyl or thienyl; (b) when m is zero, one of $R^3$ and $R^4$ is absent and the other Is hydrogen; (c) when $R^6$ or $R^7$ is attached to a carbon atom of X that is adjacent to the ring nitrogen, then $R^6$ or $R^7$, respectively, must be a substituent wherein the point of attachment is a carbon atom; and (d) when A is N, O or S, $R^9$ is not morpholin-1-yl or thiomorpholin-1-yl;

or a pharmaceutically acceptable salt of such compound.

This invention also relates to a method of treating cancer in a mammal, including a human, comprising administering to said mammal a therapeutically effective amount of an NK-1 receptor antagonist that is a compound of the formula

XVII

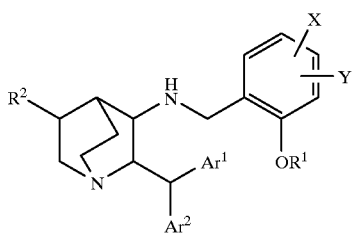

wherein $Ar^1$ and $Ar^2$ are each independently aryl or substituted aryl;

$R^1$ is alkyl having from 1 to 6 carbon atoms;

$R^2$ is hydrogen or alkyl having from 1 to 6 carbon atoms;

and either X and Y are taken separately and they are each, independently, hydrogen, dialkylphosphoryl having from 2 to 12 carbon atoms, alkyl having from 1 to 6 carbon atoms, alkenyl having from 2 to 6 carbon atoms or alkynyl having from 2 to 6 carbon atoms; or X and Y are taken together and they represent a hydrocarbon chain having 3, 4, or 5 carbon atoms, optionally containing up to 2 double bonds and optionally having 1 or 2 substituents selected from oxo, hydroxy and alkyl having from 1 to 6 carbon atoms;

provided that when X and Y are taken together they are attached to adjacent carbon atoms; and provided that if either X or Y is hydrogen, then the other one must be alkenyl or alkynyl;

or a pharmaceutically acceptable salt of such compound.

The term "alkyl" is used above for formula XVII to mean straight or branched hydrocarbon chain radicals including, but not limited to, methyl, ethyl, n-propyl, isopropyl, n-butyl, isobutyl, t-butyl, and the like.

The term "alkenyl" is used above for formula XVII to mean straight or branched hydrocarbon chain radicals having one double bond including, but not limited to, ethenyl, 1- and 2-propenyl, 2-methyl-1-propenyl, 1- and 2-butenyl and the like.

The term "alkynyl" is used above for formula XVII to mean straight or branched hydrocarbon chain radicals having one triple bond including, but not limited to, ethynyl, propynyl, butynyl and the like.

The term "aryl" is used above for formulae XVII to mean aromatic radicals including, but not limited to, phenyl, naphthyl, pyridyl, quinolyl, thienyl, furyl, oxazolyl, tetrazolyl, thiazolyl, imidazolyl, pyrazolyl and the like. There may be mentioned alkyl, alkoxy, alkylthio, halogen, cyano, nitro, phenoxy, mono- or dialkylamino and the like as the substituents on the aryl.

The term "alkoxy" is used above for formula XVII to mean —$OR^3$ ($R^3$ is alkyl) including, but not limited to, methoxy, ethoxy, propoxy, isopropoxy, n-butoxy, isobutoxy, t-butoxy and the like.

The term "halogen" is used above for formula XVII to mean radicals derived from the elements fluorine, chlorine, bromine and iodine.

The term "alkylthio" is used in formula XVII to mean —$SR^4$ ($R^4$ is alkyl) including, but not limited to, methylthio, ethylthio, n-propylthio, isopropylthio, n-butylthio, isobutylthio, t-butylthio and the like.

The term "dialkylphosphoryl" is used in formula XVII to mean —$P(O)(OR^5)(OR^6)$ ($R^5$ and $R^6$ are alkyl) including, but not limited to, diethylphosphoryl, ethylmethylphosphoryl and the like.

Other more specific embodiments of this invention relate to the method of treating cancer described immediately above, wherein the NK-1 receptor antagonist that is administered is a compound as defined in any of paragraphs (49)–(51) below, or a pharmaceutically acceptable salt of such compound.

(49) Compounds of formula XVII wherein $Ar^1$ and $Ar^2$ are each phenyl, $R^1$ is methyl, $R^2$ is hydrogen, X is alkenyl or alkynyl and Y is hydrogen.

(50) Compounds of the formula XVII wherein $Ar^1$ and $Ar^2$ are each phenyl, $R^1$ is methyl, $R^2$ is hydrogen and X and Y are each alkyl.

(51) Compounds of the formula XVII wherein $Ar^1$ and $Ar^2$ are each phenyl, $R^1$ is methyl, $R^2$ is hydrogen and X and Y represent $CH_2CH_2CH_2$ or $CH_2CH_2CH_2CH_2$.

This invention also relates to a method of treating cancer in a mammal, including a human, comprising administering to said mammal a therapeutically effective amount of an NK-1 receptor antagonist that is a compound of the formula

XVIII

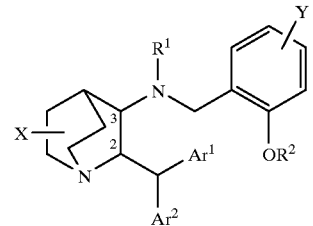

wherein $Ar^1$ and $Ar^2$ are each, independently, thienyl, phenyl, fluorophenyl, chlorophenyl or bromophenyl;

X is —$CONR^3R^4$, —$CO_2R^3$, —$CH_2OR^3$, —$CH_2NR^3R^4$ or —$CONR^3OR^4$;

$R^1$, $R^3$ and $R^4$ are each, independently, hydrogen or alkyl having 1 to 4 carbon atoms;

$R^2$ is alkyl having 1 to 4 carbon atoms;

Y is alkylsulfonyl having 1 to 4 carbon atoms, N-alkyl-N-alkanoylamino (which may be substituted by halogen in the alkanoyl moiety) having 1 to 4 carbon atoms in the alkyl and the alkanoyl moieties, N-alkyl-N-alkylsulfonylamino (which may be substituted by halogen in the alkylsulfonyl moiety) having 1 to 4 carbon atoms in the alkyl and the alkylsulfonyl moieties, alkenyl having 2 to 4 carbon atoms, alkynyl having 2 to 4 carbon atoms, halosubstituted alkyl having 1 to 4 carbon atoms, alkylamino having 1 to 4 carbon atoms, alkanoylamino (which may be substituted by halogen) having 1 to 4 carbon atoms or alkylsulfonylamino (which may be substituted by halogen) having 1 to 4 carbon atoms;

or a pharmaceutically acceptable salt of such compound.

The term "alkyl" is used above for formula XVIII to mean straight or branched hydrocarbon chain radicals including, but not limited to, methyl, ethyl, n-propyl, isopropyl, n-butyl, isobutyl, t-butyl, and the like;

The term "alkenyl" is used above for formula XVIII to mean straight or branched hydrocarbon chain radicals having one double bond including, but not limited to, ethenyl, 1- and 2-propenyl, 2-methyl-1-propenyl, 1- and 2-butenyl and the like.

The term "alkynyl" is used above for formula XVIII to mean straight or branched hydrocarbon chain radicals having one triple bond including, but not limited to, ethynyl, propynyl, butynyl and the like.

The term "alkylsulfonyl" is used above for formula XVIII to mean —$SO_2R^5$ ($R^5$ is alkyl) including, but not limited to, methylsulfonyl, ethylsulfonyl, n-propylsulfonyl, isopropylsulfonyl, n-butyl sulfonyl, isobutylsulfonyl, t-butylsulfonyl and the like.

The term "alkylamino" is used above for formula XVIII to mean —$NHR^6$ ($R^6$ is alkyl) including, but not limited to, methylamino, ethylamino, n-propylamino, isopropylamino, n-butylamino, t-butylamino and the like.

The term "alkanoylamino" is used above for formula XVIII to mean —$NHCOR^7$ ($R^7$ is alkyl or halo-substituted alkyl) including, but not limited to, formylamino, acetylamino, propionylamino, butyrylamino, isobutyrylamino, trifluoroacetylamino and the like.

the term "alkylsulfonylamino" is used above for formula XVIII to mean —$NHSO_2R^8$ ($R^8$ is alkyl or halosubstituted alkyl) including, but not limited to, methylsulfonylamino, ethylsulfonyl amino, trifluoromethylsulfonylamino and the like.

The term "N-alkyl-N-alkylsulfonylamino" is used above for formula XVIII to mean —$N(R^9)SO_2R^{10}$ ($R^9$ is alkyl and $R^{10}$ is alkyl or halosubstituted alkyl) including, but not limited to, N-methyl-N-methylsulfonylamino, N-ethyl-N-methylsulfonylamino, N-n-propyl-N-methylsulfonylamino, N-isopropyl-N-methylsulfonylamino, N-methyl-N-trifluoromethylsulfonylamino, N-ethyl-N-trifluoromethylsulfonylamino, N-n-propyl-N-trifluoromethylsulfonylamino and N-isopropyl-N-trifluoromethyl sulfonylamino.

The term "N-alkyl-N-alkanoylamino" is used above for formula XVIII to mean —$N(R^{11})COR^{12}$ ($R^{11}$ is alkyl and $R^{12}$ is alkyl or halosubstituted alkyl) including, but not limited to, N-acetyl-N-methylamino, N-acetyl-N-ethylamino, N-acetyl-N-n-propylamino, N-acetyl-N-isopropylamino, N-trifluoroacetyl-N-ethylamino, N-trifluoroacetyl-N-n-propylamino and N-trifluoroacetyl-N-isopropylamino.

Other more specific embodiments of this invention relate to the method of treating cancer described immediately above, wherein the NK-1 receptor antagonist that is administered is a compound as defined in any of paragraphs (52)–(57) below, or a pharmaceutically acceptable salt of such compound.

(52) A compound of the formula XVIII wherein $Ar^1$ and $Ar^2$ are each phenyl.

(53) A compound as described in paragraph (52) wherein $R^2$ is methyl and $R^1$ is hydrogen.

(54) A compound as described in paragraph (53) wherein X is at the 3-position of the quinuclidine ring and X is carboxy or aminocarbonyl.

(55) A compound as described in paragraph (54) wherein Y is said alkenyl.

(56) A compound as described in paragraph (55) wherein Y is isopropenyl.

(57) A compound as described in paragraph (56) wherein Y is methylsulfonyl, N-acetyl-N-methylamino or N-methyl-N-methylsulfonylamino.

This invention also relates to a method of treating cancer in a mammal, including a human, comprising administering to said mammal a therapeutically effective amount of an NK-1 receptor antagonist that is a compound of the formula

XIX

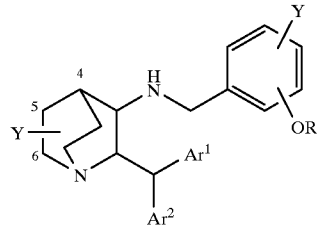

wherein R is ($C_1$–$C_6$) alkyl;

X is ($C_1$–$C_6$) alkyl having one or more substituents bonded through a heteroatom;

$Ar^1$ and $Ar^2$ are each, independently, aryl optionally substituted by one ($C_1$–$C_6$) alkyl, ($C_1$–$C_6$) alkoxy, ($C_1$–$C_6$) alkylthio, halogen, cyano, nitro, phenoxy, mono ($C_1$–$C_6$) alkylamino, di ($C_1$–$C_6$) alkylamino, halosubstituted ($C_1$–$C_6$) alkyl, or halosubstituted ($C_1$–$C_6$) alkoxy;

Y is hydrogen, ($C_1$–$C_6$) alkyl, ($C_2$–$C_6$) alkenyl, ($C_3$–$C_8$) cycloalkyl, Z—$(CH_2)_p$—, or W—$(CH_2)_m$—$CHR^2$—$(CH_2)_n$—$NR^1CO$— wherein Y is at the 4-, 5- or 6-position on the quinuclidine ring;

$R^1$ is hydrogen, ($C_1$–$C_6$) alkyl, benzyl or —$(CH_2)_r$—W;

$R^2$ is hydrogen or ($C_1$–$C_6$) alkyl which may be substituted by one hydroxy, amino, methylthio, mercapto, benzyl, 4-hydroxybenzyl, 3-indolylmethyl or —$(CH_2)_r$—W;

Z is ($C_1$–$C_6$) alkoxy, —$CONR^4R^5$, —$CO_2R^4$, —$CHR^4OR^5$, —$CHR^4NR^5R^6$, —$COR^4$, —$CONR^4OR^5$ or optionally substituted aryl;

each W is, independently, cyano, hydroxymethyl, ($C_2$–$C_6$) alkoxymethyl, aminomethyl, mono-($C_1$–$C_6$) alkylaminomethyl, di-($C_1$–$C_6$) alkylaminomethyl, carboxyl, carbamoyl or ($C_1$–$C_6$) alkoxycarbonyl;

$R^4$, $R^5$ and $R^6$ are independently hydrogen, ($C_1$–$C_6$) alkyl, ($C_1$–$C_6$) alkoxy, ($C_3$–$C_8$) cycloalkyl or an optionally substituted aryl or heterocyclic group;

p is 0 to 6; and m, n and r are each, independently, 0 to 3;

or a pharmaceutically acceptable salt of such compound.

Other more specific embodiments of this invention relate to the method of treating cancer described immediately above, wherein the NK-1 receptor antagonist that is administered is a compound as defined in any of paragraphs (58)–(60) below or a pharmaceutically acceptable salt of such compound.

(58) A compound of the formula XIX wherein X is ($C_1$–$C_6$) alkyl having one or two substituents selected from hydroxy, halogen, ($C_1$–$C_6$) alkoxy, ($C_2$–$C_6$) alkanoyl, ($C_2$–$C_6$) alkanoyloxy, ($C_1$–$C_6$) alkylthio, mono ($C_1$–$C_6$) alkylamino, di-($C_1$–$C_6$) alkylamino, amino, cyano and azido.

(59) A compound of the formula XIX as described in paragraph (58) wherein R is methyl and the OR group is at the 2-position; $Ar^1$ and $Ar^2$ are each phenyl, monochlorophenyl or monofluorophenyl; Y is hydrogen or Z—(CH$_2$)$_p$—, wherein Z is (C$_1$–C$_6$) alkoxy, —CONR$^4$R$^5$, —CO$_2$R$^4$, —CHR$^4$OR$^5$, —CHR$^4$NR$^5$R$^6$, —COR$^4$ or —CONR$^4$OR$^5$; and Y is at the 5- or 6-position.

(60) A compound as described in paragraph (59) wherein X is (C$_1$–C$_6$) alkyl having one or two substituents selected from hydroxy, (C$_1$–C$_6$) alkoxy and (C$_1$–C$_6$) alkylthio; Ar$^1$ and Ar$^2$ are each phenyl; and Y is hydrogen or carboxy.

This invention also relates to a method of treating cancer in a mammal, including a human, comprising administering to said mammal a therapeutically effective amount of an NK-1 receptor antagonist that is a compound of the formula

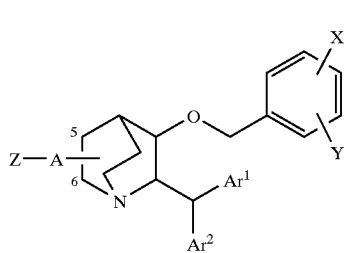

XX

W$^1$, W$^2$ and W$^3$ are each, independently, cyano, hydroxymethyl, (C$_2$–C$_5$) alkoxymethyl, aminomethyl, (C$_1$–C$_6$) alkylaminomethyl, [di(C$_1$–C$_6$) alklyamino]methyl, carboxyl, (C$_1$–C$_6$) alkylcarbamoyl, [di(C$_1$–C$_6$alkyl] carbamoyl, carbamoyl or [(C$_1$–C$_6$)alkoxy]carbonyl; and m, n, r and s are each 0, 1, 2 or 3;

or a pharmaceutically acceptable salt of such compound.

As used above for formula XX, the term "alklthio" means —S-alkyl, including but not limited to methylthio, ethylthio and the like.

As used above for formula XX, the term "alkylsulfinyl" means —SO-alkyl, including but not limited to methylsulfinyl, ethylsulfinyl, isopropylsulfinyl and the like.

As used above for formula XX, the term "alkylsulfonyl" means —SO$_2$-alkyl, including but not limited to methylsulfonyl, ethylsulfonyl, isopropylsulfonyl and the like.

As used above for formula XX, the term "aryl" means aromatic radicals including but not limited to phenyl, naphthyl, pyridyl, quinolyl, thienyl, furyl, oxazolyl, tetrazolyl, thiazolyl, imidazolyl, pyrazolyl and the like. These aryl groups can be substituted by (C$_1$–C$_6$) alkyl, (C$_1$–C$_6$)alkoxy, (C$_1$–C$_6$)alkythio, halogen, cyano, nitro, phenoxy, mono- or di-(C$_1$–C$_6$) alkylamino and the like.

This invention also relates to a method of treating cancer in a mammal, including a human, comprising administering to said mammal a therapeutically effective amount of an NK-1 receptor antagonist that is a compound of the formula

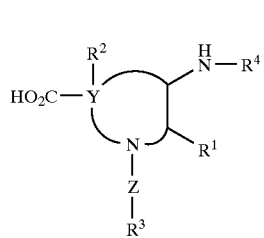

XXI wherein Y is (C$_2$–C$_4$) alkylene;

Z is a valence bond or (C$_1$–C$_6$) alkylene;

R$^1$ is phenyl, biphenyl, indanyl, naphthyl, turyl, pyridyl, thiazolyl, isothiazolyl, oxazolyl, isoxazolyl, tetrazolyl, quinolyl, phenyl (C$_1$–C$_6$)alkyl or benzhydryl, wherein each of the ring moieties may optionally be substituted by one or more substituents independently selected from halogen, (C$_1$–C$_6$)alkyl, halosubstituted (C$_1$–C$_6$)alkyl, (C$_1$–C$_6$)alkoxy and halosubstituted (C$_1$–C$_6$)alkoxy;

R$^2$ is hydrogen or (C$_1$–C$_6$)alkyl;

R$^3$ is hydrogen, hydroxy, cyano, amino or carboxy, provided that when Z is a valence bond, R$^3$ must be hydrogen;

R$^4$ represents a group of the formula (XXII) or (XXIII)

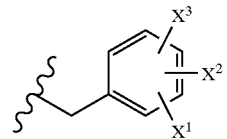

XXII

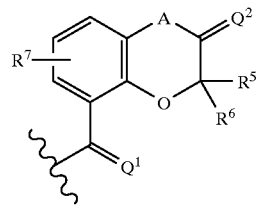

XXIII wherein X$^1$, X$^2$ and X$^3$ are each halo, hydrogen, nitro, (C$_1$–C$_6$)alkyl, halosubstituted (C$_1$–C$_6$) alkyl, (C$_1$–C$_6$) alkoxy, halosubstituted (C$_1$–C$_6$)alkoxy, hydroxy, amino, (C$_1$–C$_6$) alkylthio, (C$_1$–C$_6$)alkylsulfinyl or (C$_1$–C$_6$) alkylsulfonyl;

Q$^1$ and Q$^2$ are each H$_2$, oxygen or sulfur;

A is valence bond, methylene, oxygen, sulfur or NH;

R$^5$ and R$^6$ are each hydrogen or (C$_1$–C$_6$) alkyl; and

R$^7$ is hydrogen, halogen, C$_1$–C$_6$ alkyl, halosubstituted C$_1$–C$_6$ alkyl or C$_1$–C$_6$ alkoxy;

or a pharmaceutically acceptable salt of such compound.

The term "halo", as used above for formula XXI, includes chloro, fluoro, bromo and iodo.

The term "alkyl", as used above for formula XXI, includes saturated monovalent hydrocarbon radicals having straight, branched or cyclic moieties or combinations thereof.

The term "alkenyl", as used above for formula XXI, refers to straight or branched hydrocarbon chain radicals having one double bond including, but not limited to, ethenyl, 1- and 2-propenyl, 2-methyl-1-propenyl, 1- and 2-butenyl.

wherein X$^1$, X$^2$ and X$^3$ are each halo, hydrogen, nitro, (C$_1$–C$_6$)alkyl, halosubstituted (C$_1$–C$_6$) alkyl, (C$_1$–C$_6$) alkoxy, halosubstituted (C$_1$–C$_6$)alkoxy, hydroxy, amino, (C$_1$–C$_6$) alkylthio, (C$_1$–C$_6$)alkylsulfinyl or (C$_1$–C$_6$) alkylsulfonyl;

Q$^1$ and Q$^2$ are each H$_2$, oxygen or sulfur;

A is valence bond, methylene, oxygen, sulfur or NH;

R$^5$ and R$^6$ are each hydrogen or (C$_1$–C$_6$) alkyl; and

R$^7$ is hydrogen, halogen, C$_1$–C$_6$ alkyl, halosubstituted C$_1$–C$_6$ alkyl or C$_1$–C$_6$ alkoxy;

or a pharmaceutically acceptable salt of such compound.

The term "halo", as used above for formula XXI, includes chloro, fluoro, bromo and iodo.

The term "alkyl", as used above for formula XXI, includes saturated monovalent hydrocarbon radicals having straight, branched or cyclic moieties or combinations thereof.

The term "alkenyl", as used above for formula XXI, refers to straight or branched hydrocarbon chain radicals having one double bond including, but not limited to, ethenyl, 1- and 2-propenyl, 2-methyl-1-propenyl, 1- and 2-butenyl.

The term "alkoxy", as used above for formula XXI, refers to —O-alkyl, wherein alkyl is defined as above, and includes, but is not limited to methoxy, ethoxy, propoxy, isopropoxy, n-butoxy, isobutoxy and t-butoxy.

The term "alkylthio", as used above for formula XXI, refers to —S-alkyl, wherein alkyl is defined as above, and includes, but is not limited to methylthio, ethylthio, n-propylthio, isopropylthio, n-butylthio, isobutylthio, and t-butylthio.

The term "cycloalkyl", as used above for formula XXI, unless otherwise indicated, refers to cyclic hydrocarbon radicals including, but not limited to cyclopropyl, cyclobutyl, cyclopentyl and cyclohexyl.

The term "one or more substituents," as used above for formula XXI, includes from one to the maximum number of substituents possible based on the number of available bonding sites.

Compounds of the formulae I, X, XV, XVI, XVII, XVIII, XIX, XX and XXI contain chiral centers and therefore exist in different enantiomeric forms. The above definitions of these compounds include all optical isomers and all stereoisomers of such compounds, and mixtures thereof.

Other more specific embodiments of this invention relate to any of the above methods of treating cancer, wherein the NK-1 receptor antagonist that is administered is selected from the group consisting of:

(2S,3S)-3-(5-tert-butyl-2-methoxybenzyl)amino-2-(3-trifluoromethoxyphenyl)piperidine;

(2S,3S)-3-(2-isopropoxy-5-trifluoromethoxybenzyl)amino-2-phenylpiperidine;

(2S,3S)-3-(2-ethoxy-5-trifluoromethoxybenzyl)amino-2-phenylpiperidine;

(2S,3S)-3-(2-methoxy-5-trifluoromethoxybenzyl)amino-2-phenylpiperidine;

(2S,3S)-3(-5-tert-butyl-2-trifluoromethoxybenzyl)amino-2-phenylpiperidine;

2-(diphenylmethyl)-N-(2-methoxy-5-trifluoromethoxyphenyl)methyl-1-azabicyclo[2.2.2]octan-3-amine;

(2S,3S)-3-[5-chloro-2-(2,2,2-trifluoroethoxy)benzyl]amino-2-phenylpiperidine;

(2S,3S)-3-(5-tert-butyl-2-trifluoromethoxybenzyl)amino-2-phenylpiperidine;

(2S,3S)-3-(2-isopropoxy-5-trifluoromethoxybenzyl)amino-2-phenylpiperidine;

(2S,3S)-3-(2-difluoromethoxy-5-trifluoromethoxybenzyl)amino-2-phenylpiperidine;

(2S,3S)-2-phenyl-3-[2-(2,2,2-trifluoroethoxybenzyl)aminopiperidine;

(2S,3S)-2-phenyl-3-(2-trifluoromethoxybenzyl)aminopiperidine;

cis-3-(2-chlorobenzylamino)-2-phenylpiperidine;

cis-3-(2-trifluoromethylbenzylamino)-2-phenyl- piperidine;

cis-3-(2-methoxybenzylamino)-2-(2-fluorophenyl)piperidine;

cis-3-(2-methoxybenzylamino)-2-(2-chlorophenyl)piperidine;

cis-3-(2-methoxybenzylamino)-2-(2-methylphenyl)piperidine;

cis-3-(2-methoxybenzylamnino)-2-(3-methoxyphenyl)piperidine;

cis-3-(2-methoxybenzylamino)-2-(3-fluorophenyl)piperidine;

cis-3-(2-methoxybenzylamino)-2-(3-chlorophenyl)piperidine;

cis-3-(2-methoxybenzylamino)-2-(3-methylphenyl)piperidine;

cis-3-(2-methoxybenzylamino)-2-(4-fluorophenyl)piperidine;

cis-3-(2-methoxybenzylamino)-2-(3-thienyl)piperidine;

cis-3-(2-methoxybenzylamino)-2-phenylazacycloheptane;

3-(2-methoxybenzylamino)-2-methyl-2-phenylpiperidine;

3-(2-methoxybenzylamino)-5-methyl-2-phenylpiperidine;

(2S,3S)-1-(5-carboethoxypent-1-yl)-3-(2-methoxybenzylamino)-2-phenylpiperidine;

(2S,3S)-1-(6-hydroxyhex-1-yl)-3-(2-methoxybenzylamino)-2-phenylpiperidine;

(2S,3S)-1-(4-hydroxy-4-phenylbut-1-yl)-3-(2-methoxybenzylamino)-2-phenylpiperidine;

(2S,3S)-1-(4-oxo-4-phenylbut-1-yl)-3-(2-methoxybenzylamino)-2-phenylpiperidine;

(2S,3S)-1-(5,6-dihydroxyhex-1-yl)-3-(2-methoxybenzylamino)-2-phenylpiperidine;

cis-3-(5-fluoro-2-methoxybenzylamino)-2-phenylpiperidine;

(2S,3S)-1-[4-(4-fluorophenyl)-4-oxobut-1-yl]-3-(2-methoxybenzylamino)-2-phenylpiperidine;

(2S,3S)-1-[4-[4-fluorophenyl)-4-hydroxybut-1-yl]-3-(2-methoxybenzylamino)-2-phenylpiperidine;

cis-3-(2-methoxy-5-methylbenzylamino)-2-phenylpiperidine;

(2S,3S)-1-(4-benzamidobut-1-yl)-3-(2-methoxybenzylamino)-2-phenylpiperidine;

cis-3-(2-methoxynaphth-1-ylmethylamino)-2-phenylpiperidine;

(2S,3S)-3-(2-methoxybenzylamino)-1-(5-N-methylcarboxamidopent-1-yl)-2-phenylpiperidine;

(2S,3S)-1-(4-cyanobut-1-yl)-3-(2-methoxybenzylamino)-2-phenylpiperidine;

(2S,3S)-1-[4-(2-naphthamido)but-1-yl]-3-(2-methoxybenzylamino)-2-phenylpiperidine;

(2S,3S)-1-(5-benzamidopent-1-yl)(2-methoxybenzylfamino)-2-phenylpiperidine;

(2S,3S)-1-(5-aminopent-1-yl)-3-(2-methoxybenzylamino)-2-phenylpiperidine;

(2S,3S)-(5-chloro-2-methoxybenzylamino)-2-phenylpiperidine;

(2S,3S)-3-(2,5-dimethoxybenzylamino)-2-phenylpiperidine;

cis-3-(3,5-difluoro-2-methoxybenzylamino)-2-phenylpiperidine;

cis-3-(4,5-difluoro-2-methoxybenzylamino)-2-phenylpiperidine;

cis-3-(2,5-dimethoxybenzylamino)-1-[4-(4-fluorophenyl)-4-oxobut-1-yl]-2-phenylpiperidine;

cis-3-(5-chloro-2-methoxybenzylamino)-1-(5,6-dihydroxyhex-1-yl)-2-phenylpiperidine;

cis-1-(5,6-dihydroxyhex-1-yl)-3-(2,5-dimethoxybenzylamino)-2-phenylpiperidine;

cis-2-phenyl-3-[2-(prop-2-yloxy)benzylamino]piperidine;

cis-3-(2,5-dimethoxybenzyl)amino-2-(3-methoxyphenyl)piperidine;

cis-3-(5-chloro-2-methoxybenzyl)amino-2-(3-methoxyphenyl)piperidine;

cis-3-(5-chloro-2-methoxybenzyl)amino-2-(3-chlorophenyl)piperidine;

3-(2-methoxybenzylamino)-2,4-diphenylpiperidine;

cis-3-(2-methoxybenzylamino)-2-phenylpyrrolidine;

(2S,3S)-3-(5-ethyl-2-methoxybenzyl)amino-2-phenylpiperidine;

(2S,3S)-3-(5-n-butyl-2-methoxybenzyl)amino-2-phenylpiperidine;

(2S,3S)-3-(2-methoxy-5-n-propylbenzyl)amino-2-phenylpiperidine;

(2S,3S)-3-(5-isopropyl-2-methoxybenzyl)amino-2-phenylpiperidine;

(2S,3S)-3-(5-s-butyl-2-methoxybenzyl)amino-2-phenylpiperidine;

(2S,3S)-3-(5-t-butyl-2-methoxybenzyl)amino-2-phenylpiperidine;

(2S,3S)-3-(2-methoxy-5-phenylbenzyl)amino-2-phenylpiperidine;

2,4-dimethylthiazole-5-sulfonic acid [4-methoxy-3-((2S,3S)-2-phenylpiperidin-3-ylaminomethyl)phenyl]methylamide;

N-(4,5-dimethylthiazol-2-yl)-N-[4-methoxy-3-((2S,3S)-2-phenylpiperidin-3-yl-aminomethyl)phenyl]methanesulfonamide;

{5-[(4,5-dimethylthiazol-2-yl)methylamino]-2-methoxybenzyl}-((2S,3S)-2-phenylpiperidin-3-yl)amine;

{5-(4,5-dimethylthiazol-2-ylamino)-2-methoxybenzyl}-((2S,3S)-2-phenylpiperidin-3-ylamine;

4,5-dimethylthiazole-2-sulfonic acid methyl-[3-((2S,3S)-2-phenylpiperidin-3-ylaminomethyl)-4-trifluoromethoxyphenyl]-amide;

2,4-dimethylthiazole-5-sulfonic acid [4-isopropoxy-3-((2S,3S)-2-phenylpiperidin-3-ylaminomethyl)phenyl]-methylamide;

2,4-dimethylthiazole-5-sulfonic acid [4isopropoxy-3-((2S,3S)-2-phenylpiperidin-3-ylaminomethyl)phenyl]-isopropylamide;

2,4-dimethylthiazole-5-sulfonic acid [4methoxy-3-((2S,3S)-2-phenylpiperidin-3-ylaminomethyl)phenyl]-isopropylamide;

2,4dimethylthiazole-5-sulfonic acid [4-methoxy-3-((2S,3S)-2-phenylpiperidin-3-ylaminomethyl)phenyl]-isobutylamide;

2,4-dimethylthiazole-5-sulfonic acid [4-isopropoxy-3-((2S,3S)-2-phenylpiperidin-3-ylaminomethyl)phenyl]-isobutylamide;

(2S,3S)-N-(5-isopropyl-2-methoxyphenyl)methyl-2-diphenylmethyl-1-azabicyclo-[2.2.2]octan-3-amine;

(2S,3S)-N-(5-tert-butyl-2-methoxyphenyl)methyl-2-diphenylmethyl-1-azabicyclo[2.2.2]octan-3-amine;

(2S,3S)-N-(5-methyl-2-methoxyphenyl)methyl-2-diphenylmethyl-1-azabicyclo[2.2.2]octan-3-amine;

(2S,3S)-N-(5-ethyl-2-methoxyphenyl)methyl-2-diphenylmethyl-1-azabicyclo[2.2.2]octan-3-amine;

(2S,3S)-N-(5-isopropyl-2-methoxyphenyl)methyl-2-diphenylmethyl-1-azabicyclo[2.2.2]octan-3-amine;

(2S,3S)-N-(5-sec-butyl-2-methoxyphenyl)methyl-2-diphenylmethyl-1-azabicyclo[2.2.2]octan-3-amine;

(2S,3S)-N-(5-n-propyl-2-methoxyphenyl)methyl-2-diphenylmethyl-1-azabicyclo[2.2.2]octan-3-amine;

(2S,3S)-2-diphenylmethyl-3-(5-tert-butyl-2-methoxybenzyl)amino-1-azabicyclo[2.2.2]octane;

(2S,3S)-N-[5-(1-cyano-1-methylethyl)-2-methoxybenzyl]-2-phenylpiperidine-3-amine;

(2S,3S)-3-(6-methoxy-1-methyl-2-oxo-1,2,3,4-tetrahydroquinolin-7-yl)methyl-2-phenylpiperidine-3-amine;

(2S,3S)-2-phenyl-N-[5-[2,2,2-trifluoro-1-(trifluoromethyl)ethyl]-2-methoxybenzyl]piperidine-3-amine;

(2S,3S)-2-diphenylmethyl-N-[2-methoxy-5-(methylsulfonyl)benzyl]-1-azabicyclo[2.2.2]octane-3-amine;

(2S,3S)-2-diphenylmethyl-N-(5-isopropenyl-2-methoxybenzyl)-1-azabicyclo[2.2.2]octane-3-amine;

(2S,3S)-2-diphenylmethyl-N-[5-(1-hydroxy-1-methylethyl)-2-methoxybenzyl]-1-azabicyclo[2.2.2]octane-3-amine;

(3R,4S,5S,6S)-N,N-diethyl-5-(5-isopropyl-2-methoxybenzylamino)-6-diphenylmethyl-1-azabicyclo[2.2.2]octane-3-carboxamide;

(3R,4S,5S,6S)-N,N-diethyl-5-(2,5-dimethoxybenzylamino)-6-diphenylmethyl-1-azabicyclo[2.2.2]octane-3-carboxamide;

(3R,4S,5S,6S)-5-(5-isopropyl-2-methoxybenzylamino)-6-diphenylmethyl-1-azabicyclo[2.2.2]octane-3-carboxylic acid;

(3R,4S,5S,6S)-5-(2-methoxy-2-methylthiobenzylamino)-6-diphenylmethyl-1-azabicyclo[2.2.2]octane-3-carboxylic acid;

(3R,4S,5S,6S)-5-(2,5-dimethoxybenzylamino)-6-diphenylmethyl-1-azabicyclo-[2.2.2]octane-3-carboxylic acid;

(3R,4S,5S,6S)-5-(2-methoxy-5-methylbenzylamino)-6-diphenylmethyl-1-azabicyclo[2.2.2]octane-3-carboxylic acid;

(3R,4S,5S,6S)-5-(5-ethyl-2-methoxybenzylamino)-6-diphenylmethyl-1-azabicyclo[2.2.2]octane-3-carboxylic acid;

(3R,4S,5S,6S)-5-(2-methoxyl-5-n-propylbenzylamino)-6-diphenylmethyl-1-azabicyclo[2.2.2]octane-3-carboxylic acid;

(3R,4S,5S,6S)-5-(5-sec-butyl-2-methoxybenzylamino)-6-diphenylmethyl-1-azabicyclo[2.2.2]octane-3-carboxylic acid;

(3R,4S,5S,6S)-5-(5-N-methyl-methanesulfonylamino-2-methoxybenzylamino)-6-diphenylmethyl-1-azabicyclo[2.2.2]octane-3-carboxylic acid;

(3R,4S,5S,6S)-5-(2-methoxy-5-methylsulfinylbenzylamino)-6-diphenylmethyl-1-azabicyclo[2.2.2]octane-3-carboxylic acid;

(3R,4S,5S,6S)-5-(2-methoxy-trifluoromethoxybenzylamino)-6-diphenylmethyl-1-azabicyclo[2.2.2]octane-3-carboxylic acid;

(3R,4S,5S,6S)-5-(2-methoxy-5-methylsulfonylbenzylamino)-6-diphenylmethyl-1-azabicyclo[2.2.2]octane-3-carboxylic acid;

(3R,4S,5S,6S)-5-(5-dimethylamino-2-methoxybenzylamino)-6-diphenylmethyl-1-azabicyclo[2.2.2]octane-3-carboxylic acid;

(3R,4S,5S,6S)-5-(5-isopropyl-2-methoxybenzylamino)-6-diphenylmethyl-1-azabicyclo[2.2.2]octane-2-carboxylic acid;

(3R,4S,5S,6S)-5-(2-methoxy-5-methylthiobenzylamino)-6-diphenylmethyl-1-azabicyclo[2.2.2]octane-2-carboxylic acid;

(3R,4S,5S,6S)-5-(2,5-dimethoxybenzylamino)-6-diphenylmethyl-1-azabicyclo[2.2.2]octane-2-carboxylic acid;

(3R,4S,5S,6S)-5-(2-methoxy-5-methylbenzylamino)-6-diphenylmethyl-1-azabicyclo[2.2.2]octane-2-carboxylic acid;

(3R,4S,5S,6S)-5-(5-ethyl-2-methoxybenzylamino)-6-diphenylmethyl-1-azabicyclo[2.2.2]octane-2-carboxylic acid;

(3R,4S,5S,6S)-5-(2-methoxyl-5-n-propylbenzylamino)-6-diphenylmethyl-1-azabicyclo[2.2.2]octane-2-carboxylic acid;

(3R,4S,5S,6S)-5-(5-sec-butyl-2-methoxybenzylamino)-6-diphenylmethyl-1-azabicyclo[2.2.2]octane-2-carboxylic acid;

(3R,4S,5S,6S)-5-(5-N-methyl-methanesulfonylamino-2-methoxybenzylamino)-6-diphenylmethyl-1-azabicyclo[2.2.2]octane-2-carboxylic acid;

(3R,4S,5S,6S)-5-(2-methoxy-5-methylsulfinyl-benzylamino)-6-diphenylmethyl-1-azabicyclo[2.2.2]octane-2-carboxylic acid;

(3R,4S,5S,6S)-5-(2-methoxy-trifluoromethoxy-benzylamino)-6-diphenylmethyl-1-azabicyclo[2.2.2]octane2-carboxylic acid;

(3R,4S,5S,6S)-5-(2-methoxy-5-methylsulfonyl-benzylamino)-6-diphenylmethyl-1-azabicyclo[2.2.2]octane-2-carboxylic acid; and (3R,4S,5S,6S)-5-(5-dimethylamino-2-methoxy-benzylamino)-6-diphenylmethyl-1-azabicyclo[2.2.2]octane-2-carboxylic acid;

and the pharmaceutically acceptable salts of the foregoing compounds.

DETAILED DESCRIPTION OF THE INVENTION

The compounds of the formulae Ia, Ib, Ic, Id, Ie, X, XV, XVI, XVII, XVIII, XIX, XX and XXI may be prepared as described below. Unless otherwise indicated, in the discussion that follows, structural formulae Ia, Ib, Ic, Id, Ie, X, XV, XVI, XVII, XVIII, XIX, XX and XXI and groups II, III, IV, V, VI, VII, VIII, IX, XXII and XXIII are defined as above.

Compounds of the formula Ia and Ib may be prepared as described in U.S. Ser. No. 08/522,230, filed Oct. 7, 1993, corresponding to EP 675,886 and EP 806,423; which is a continuation-in-part of U.S. patent application Ser. No. 988,653, which was filed on Dec. 10, 1992, now abandoned. These applications are incorporated herein by reference in their entirety.

Compounds of the formula Ic may be prepared as described in U.S. Ser. No. 08/387,765, filed May 5, 1993, now U.S. Pat. No. 5,721,255 corresponding to EP 655,996; which is a continuation-in-part of U.S. patent application Ser. No. 932,392, which was filed on Aug. 19, 1992, now abandoned and PCT Patent Application PCT/US 93/09407, which designates the United States and which was filed in the United States Receiving Office on Oct. 7, 1993 and published as WO 94/13663 on Jun. 23, 1994. These applications and patents are incorporated herein by reference in their entirety.

Compounds of the formula Id may be prepared as described in U.S. Ser. No. 08/443,418, filed May 22, 1995, now U.S. Pat. No. 5,744,480; which is a division of U.S. Ser. No. 08/167,881, filed May 5, 1992, now U.S. Pat. No. 5,773,450 corresponding to EP 589,924; which is a continuation-in-part of U.S. Ser No. 717,943, filed Jun. 20, 1991, now abandoned; and in PCT Patent Application PCT/US 92/03571, which designates the United States and which was filed in the United States Receiving Office on May 5, 1992 and published as WO 93/00331 on Jan. 7, 1993. These applications and patents are incorporated herein by reference in its entirety.

Compounds of the formula Ie may be prepared as described in U.S. Ser. No. 08/615,257, filed Jul. 18, 1994, now U.S. Pat. No. 5,703,065 corresponding to EP 719,266; which is a continuation of U.S. patent application Ser. No. 123,306, which was filed on Sep. 17, 1993, now abandoned and in PCT Patent Application PCT/IB 94/00221, which designates the United States and which was filed in the International Bureau on Jul. 18, 1994 and was published as WO 95/07908 on Mar. 23, 1995. These applications and patents are incorporated herein by reference in its entirety.

When $R^3$ is a group of the formula II, the starting materials of the formula $NH_2R^3$ that are used in the preparation of compounds of the formulae Ia, Ib, Ic, Id and Ie may be prepared as described in U.S. Pat. No. 5,162,339, which issued on Nov. 11, 1992 and corresponds to EP 409,931; in PCT Application PCT/US 88/04205 designating the United States, filed in the U.S. Receiving Office on Nov. 23, 1988 and published as WO 90/05525 on May 31, 1990; and in PCT Application PCT/US 89/05338 designating the United States, filed in the U.S. Receiving Office on Nov. 20, 1989 and published as WO 90/05729 on May 31, 1990. This patent and these applications are incorporated herein by reference in their entirety.

When $R^3$ is a group of the formula III, the starting materials of the formula $NH_2R^3$ that are used in the preparation of compounds of the formulae Ia, Ib, Ic, Id and Ie may be prepared as described in U.S. Ser. No. 07/955,733, filed Apr. 25, 1991, now U.S. Pat. No. 5,451,586 corresponding to EP 532,527; which is a continuation-in-part of U.S. Ser. No. 532,525, filed Jun. 1, 1990, now abandoned; and in PCT Patent Application PCT/US 91102853, which designates the United States, was filed in the United States Receiving Office on Apr. 25, 1991 and was published as WO 91/18899 on Dec. 12, 1991. These applications and patents are incorporated herein by reference in their entirety.

When $R^3$ is a group of the formula IV, V or VI, the starting materials of the formula $NH_2R^3$ that are used in the preparation of compounds of the formulae Ia, Ib, Ic, Id and Ie may be prepared as described in U.S. Ser. No. 08/403,967, filed Mar. 14, 1995, now U.S. Pat. No. 5,698,568 and in U.S. Ser. No. 08/403,987, filed Mar. 14, 1992, now U.S. Pat. No. 5,641,786, both of which are divisions of U.S. Ser No. 07/988,125, filed May 14, 1991 now U.S. Pat. No. 5,422,354; which is a continuation-in-part of U.S. Ser. No. 557,442, filed Jul. 23, 1990, now abandoned; and in PCT Patent Application PCT/US 91/03369, which designates the United States, was filed in the United States Receiving Office on May 14, 1991 and was published as WO 92/01688 on Feb. 6, 1992. These applications and patents are incorporated herein by reference in their entirety.

When $R^3$ is a group of the formula VII, the starting materials of the formula $NH_2R^3$ that are used in the preparation of compounds of the formulae Ia, Ib, Ic, Id and Ie may be prepared as described in U.S. Ser. No. 08/014,970, filed Feb. 8, 1993, now U.S. Pat. No. 5,332,817; which is a division of U.S. Ser. No. 724,268, filed Jul. 1, 1991, now U.S. Pat. No. 5,232,929 corresponding to EP 594,636; which is a continuation-in-part of U.S. Ser. No. 619,361, filed Nov. 28, 1990, now abandoned; in PCT Application PCT/US 90/00116 designating the United States, filed in the U.S. Receiving Office on Jan. 4, 1990 and published as WO 91/09844 on Jul. 11, 1991; and in PCT Application PCT/US 92/04008 designating the United States, filed in the U.S. Receiving Office on May 21, 1992 and published as WO 93/01170 on Jan. 21, 1993; U.S. Ser. No. 08/273,662, filed Jul. 12, 1994, now U.S. Pat. No. 5,663,349; which is a continuation of U.S. Ser. No. 07/800,667, filed Nov. 27, 1991, now U.S. Pat. No. 5,364,943; which is a continuation-in-part of U.S. Ser No. 531,265, filed May 31, 1990, now abandoned; in PCT Patent Application PCT/US 91/02541, which designates the United States, was filed in the United States Receiving Office on Apr. 12, 1991 and was published as WO 91/18878 on Dec. 12, 1991, corresponding to EP 532,515; in PCT Application PCT/US 92/09929 designating the United States, filed in the U.S. Receiving Office on Nov. 24, 1992 and published as WO 93/11110 on Jun. 10, 1993; and in U.S. Ser. No. 08/119,149, filed Jan. 14, 1992, now U.S. Pat. No. 5,686,615; which is a continuation of U.S. Ser. No. 675,244, filed Mar. 26, 1991, now abandoned; and PCT Patent Application PCT/US 92/00065, which designates the United States, was filed in the United States Receiving Office on Jan. 14, 1992 and was published as WO 92/17449 on Oct. 15, 1992. These applications and patents are incorporated herein by reference in their entirety.

When $R^3$ is a group of the formula VIII, the starting materials of the formula $NH_2R^3$ that are used in the preparation of compounds of the formulae Ia, Ib, Ic, Id and Ie may be prepared as described in PCT Patent Application PCT/US 91/05776, which designates the United States, was filed in the United States Receiving Office on Aug. 20, 1991 and was published as WO 92/06079 on Apr. 16, 1992, above-mentioned U.S. Ser. No. 08/273,662 and applications related thereto; and above-mentioned PCT/US 92/00065 and applications related thereto. These applications and patents are incorporated herein by reference in their entirety.

When $R^3$ is a group of the formula IX, the starting materials of the formula $NH_2R^3$ that are used in the preparation of compounds of the formulae Ia, Ib, Ic, Id and Ie may be prepared as described in U.S. Ser. No. 08/167,851, filed Jun. 11, 1992, now U.S. Pat. No. 5,604,252 corresponding to EP 591,333; which is a continuation-in-part of U.S. Ser No. 719,884, filed Jun. 21, 1991, now abandoned; and in PCT Patent Application PCT/US 92/04697, which designates the United States and which was filed in the United States Receiving Office on Jun. 11, 1992 and published as WO 93/00330 on Jan. 7, 1993. These applications and patents are incorporated herein by reference in their entirety.

Compounds of the formula X may be prepared as described in U.S. Ser. No. 08/175,353, filed May 18, 1992, now U.S. Pat. No. 5,716,965 corresponding to EP 585,328; and in PCT Patent Application PCT/US 92/04002, which designates the United States, was filed in the United States Receiving Office on May 19, 1992 and was published as WO 92/20676 on Nov. 26, 1992. This application is incorporated herein by reference in its entirety.

Compounds of the formula XV may be prepared by the procedure described in PCT Patent Application PCT/US 92/04002, which designates the United States, was filed on May 19, 1992 and published as WO 92/20676 on Nov. 26, 1992. This application is incorporated herein by reference in its entirety.

Compounds of the formula XVI may be prepared as described in U.S. Ser. No. 08/513,798, filed Dec. 10, 1993, now U.S. Pat. No. 5,688,806 corresponding to EP 687,268; which is a continuation-in-part of U.S. Ser No. 026,382, filed Mar. 4, 1993, now abandoned; and in PCT Patent Application PCT/US 93/11793, which designates the United States, and which was filed on Dec. 10, 1993 in the U.S. Receiving Office and published as WO 94/20500 on Sep. 15, 1994. These applications and patents are incorporated herein by reference in their entirety.

Compounds of the formula XVII may be prepared as described in U.S. Ser. No. 08/428,240, filed Sep. 30, 1993, corresponding to EP 665,843; and in PCT Patent Application PCT/US 93/09169, which designates the United States and which was filed in the U.S. Receiving Office on Sep. 30, 1993 and published as WO 94/10170 on May 11, 1994. These applications are incorporated herein by reference in its entirety.

Compounds of the formula XVIII may be prepared as described in U.S. Ser. No. 08/416,913, filed Sep. 30, 1993, now U.S. Pat. No. 5,604,241 corresponding to EP 665,844; and in PCT Patent Application PCT/US 93/09168, which designates the United States and which was filed in the U.S. Receiving Office on Sep. 30, 1993 and published as WO 94/08997 on Apr. 28, 1994. These applications are incorporated herein by reference in their entirety.

Compounds of the formula XIX may be prepared as described in U.S. Ser. No. 08/556,916, filed May 13, 1994, now U.S. Pat. No. 5,741,797 corresponding to EP 699,199; and in PCT Patent Application PCT/JP 94/00781, which designates the United States and which was filed in the Japanese Receiving Office on May 13, 1994. This application is incorporated herein by reference in its entirety.

Compounds of the formula XX may be prepared as described in U.S. Ser. No. 08/637,682, filed Jul. 5, 1994; and in PCT Patent Application PCT/JP 94/01092, which designates the United States and was filed in the Japanese Receiving Office on Jul. 5, 1994. These applications are incorporated herein by reference in their entirety.

Compounds of the formula XXI may be prepared as described in U.S. Ser. No. 08/957,176, filed Oct. 24, 1997, which is a continuation of U.S. Ser. No. 08/617,896, filed Sep. 13, 1994, corresponding to EP 719,253, now abandoned; and in PCT Patent Application PCT/JP 94/01514, which designates the United States and was filed in the Japanese Receiving Office on Sep. 13, 1994. These application are incorporated herein by reference in their entirety.

The therapeutic agents that are basic in nature are capable of forming a wide variety of different salts with various inorganic and organic acids. Examples of acids that form suitable pharmaceutically acceptable salts for use in this invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

Although such salts must be pharmaceutically acceptable for administration to animals, it is often desirable in practice to initially isolate a therapeutic agent from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base therapeutic agents of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those therapeutic agents of this invention that are also acidic in nature are capable of forming base salts with various pharmacologically acceptable cations. The chemical bases that are used as reagents to prepare the pharmaceutically acceptable base salts of the therapeutic agents are those that form non-toxic base salts with the acidic therapeutic agents. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The following references refer, collectively, to quinuclidine, piperidine, ethylene diamine, pyrrolidine and azanorbomane derivatives and related compounds that exhibit activity as substance P receptor antagonists and can therefore be employed in the methods of this invention, and to methods of preparing the same: U.S. Pat. Nos. 5,162,339, which issued on Nov. 11, 1992; 5,232,929, which issued on Aug. 3, 1993; World Patent Application WO 92/20676, published Nov. 26, 1992; World Patent Application WO 93/00331, published Jan. 7, 1993; World Patent Application WO 92/21677, published Dec. 10, 1992; World Patent Application WO 93/00330, published Jan. 7, 1993; World Patent Application WO 93/06099, published Apr. 1, 1993; World Patent Application WO 93/10073, published May 27, 1993; World Patent Application WO 92/06079, published Apr. 16, 1992; World Patent Application WO 92/12151, published Jul. 23, 1992; World Patent Application WO 92/15585, published Sep. 17, 1992; World Patent Application WO 93/10073, published May 27, 1993; World Patent Application WO 93/19064, published Sep. 30, 1993; World Patent Application WO 94/08997, published Apr. 28, 1994; World Patent Application WO 94/04496, published Mar. 3, 1994; World Patent Application WO 94/13663, published Jun. 23, 1994; World Patent Application WO 94/20500, published Sep. 15, 1994; World Patent Application PCT/ IB94/00221, which designates the United States and was filed on Jul. 18, 1994; World Patent Application PCT/JP94/ 00781, which designates the United States and was filed on May 13, 1994; World Patent Application PCT/JP94/01092, which designates the United States and was filed on Jul. 5, 1994; and World Patent Application PCT/JP94/01514, which designates the United States and was filed on Sep. 13, 1994. All of the foregoing World Patent Applications designate the United States. The foregoing patents and patent applications are incorporated herein by reference in their entirety.

The specific NK-1 receptor antagonists listed in the Summary of the Invention can be prepared by methods described in the published patents and patent applications listed above, as well as in the scientific literature.

Other NK-1 receptor antagonists that can be employed in the methods of this invention are those compounds and pharmaceutically acceptable salts described in the following references: European Patent Application EP 499,313, published Aug. 19, 1992; European Patent Application EP 520,555, published Dec. 30, 1992; European Patent Application EP 522,808, published Jan. 13,1993, European Patent Application EP 528,495, published Feb. 24, 1993, PCT Patent Application WO 93/14084, published Jul. 22, 1993, PCT Patent Application WO 93/01169, published Jan. 21, 1993, PCT Patent Application WO 93/01165, published Jan. 21, 1993, PCT Patent Application WO 93/01159, published Jan. 21, 1993, PCT Patent Application WO 92/20661, published Nov. 26, 1992, European Patent Application EP 517,589, published Dec. 12, 1992, European Patent Application EP 428,434, published May 22, 1991, European Patent Application EP 360,390, published Mar. 28, 1990, PCT Patent Application WO 95/19344, published Jul. 20, 1995, PCT Patent Application WO 95/23810, published Sep. 8, 1995, PCT Patent Application WO 95/20575, published Aug. 3, 1995 and PCT Patent Application WO 95/28418, published Oct. 26, 1995.

Generally, in carrying out the methods of this invention, the NK-1 receptor antagonist will be administered to an adult human In an amount ranging from about 0.07 to about 21 mg per kg body weight of the subject being treated per day, in single or divided doses, preferably from about 0.36 to about 4.3 mg/kg. Variations may nevertheless occur depending upon the species of the subject being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The NK-1 receptor antagonists and their pharmaceutically acceptable salts that are employed in the methods of this Invention are hereinafter also referred to as the "therapeutic agents". The therapeutic agents can be administered via either the oral or parenteral route.

The therapeutic agents may be administered alone or in combination with pharmaceutically acceptable carriers or diluents by either of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention are present In such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic agent in either sesame or peanut oil or in aqueous propylene glycol may be employed. The aqueous solutions should be suitably buffered if necessary and the liquid diluent first rendered isotonic. These aqueous solutions are suitable for Intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The activity of certain therapeutic agents as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al.. as reported in the *Journal of Biological Chemistry, Vol.* 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 µg/ml of bacitracin, 4 µg/ml of leupeptin, 2 µg of chymostatin and 200 µg/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (a. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The ability of the NK-1 receptor antagonists used in the methods of this invention to inhibit the proliferation of small cell lung carcinoma cells can be determined using the in vivo and in vitro cell proliferation assays described by Orosz et al., *International Journal of Cancer,* 1995, 60, 82–87, and by Bunn et al., *Cancer Research,* 1994, 54, 3602–3610.

I claim:

1. A method of treating small cell lung carcinoma, extra-pulmonary small cell carcinoma or neuroendocrine tumor in a mammal in need of such treatment, comprising administering to said mammal a therapeutically effective amount of an NK-1 receptor antagonist comprising (3R,4S,5S,6S)-5-(2,5-dimethoxybenzylamino)-6-diphenylmethyl-1-azabicyclo[2.2.2.]octane-3-carboxylic acid, or a pharmaceutically acceptable salt of said compound.

* * * * *